United States Patent
Nishikawa et al.

(10) Patent No.: US 12,203,851 B2
(45) Date of Patent: Jan. 21, 2025

(54) METHOD FOR DETECTING OBJECTIVE SUBSTANCE

(71) Applicant: FUJIFILM Corporation, Tokyo (JP)

(72) Inventors: Naoyuki Nishikawa, Ashigara-kami-gun (JP); Yoshihiro Aburaya, Ashigara-kami-gun (JP); Kenichi Moriwaki, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 905 days.

(21) Appl. No.: 17/153,663

(22) Filed: Jan. 20, 2021

(65) Prior Publication Data

US 2021/0148820 A1    May 20, 2021

Related U.S. Application Data

(63) Continuation of application No. PCT/JP2019/033145, filed on Aug. 23, 2019.

(30) Foreign Application Priority Data

Aug. 23, 2018 (JP) ................. 2018-156617

(51) Int. Cl.
G01N 21/64    (2006.01)
G01N 33/543    (2006.01)

(52) U.S. Cl.
CPC ... G01N 21/6428 (2013.01); G01N 33/54326 (2013.01)

(58) Field of Classification Search
CPC ......... G01N 21/6428; G01N 33/54326; G01N 2021/6441
See application file for complete search history.

(56) References Cited

U.S. PATENT DOCUMENTS

2015/0051102 A1* 2/2015 Fu .............................. B03C 1/01
506/13
2015/0344937 A1    12/2015 Flor et al.
(Continued)

FOREIGN PATENT DOCUMENTS

JP    2017-219512 A    12/2017
JP    2020-30136 A    2/2020
(Continued)

OTHER PUBLICATIONS

International Preliminary Report on Patentability and Written Opinion of the International Searching Authority (Forms PCT/IB/326, PCT/IB/373 and PCT/ISA/237) for corresponding International Application No. PCT/JP2019/033145, dated Mar. 4, 2021, with English translation of the Written Opinion.

(Continued)

Primary Examiner — Dennis White
(74) Attorney, Agent, or Firm — Birch, Stewart, Kolasch & Birch, LLP

(57) ABSTRACT

An object of the invention is to provide a method for detecting an objective substance, by which a plurality of kinds of objective substances can be detected by a single detection, in the detection of an objective substance from an analyte by utilizing magnetic force. In a case where an objective substance is detected by causing magnetic particles and labeling particles to bind to an objective substance and causing a conjugate thereof to move by magnetic force, the object is addressed by using a plurality of labeling particles including first labeling particles that bind to at least a first objective substance, and second labeling particles that bind to the first objective substance and bind to an objective substance to which the first labeling particles do not bind; and detecting an objective substance with a combination of bound labeling particles, the labeling particles satisfying at least one of a first condition that the particle sizes are (Continued)

different or a second condition that the signal lights generated upon light irradiation are different.

13 Claims, 7 Drawing Sheets

(56) References Cited

U.S. PATENT DOCUMENTS

| | | | |
|---|---|---|---|
| 2017/0160272 A1* | 6/2017 | Tsao | ..................... G03F 7/0041 |
| 2019/0085385 A1 | 3/2019 | Makino et al. | |
| 2019/0154580 A1 | 5/2019 | Yasuura et al. | |

FOREIGN PATENT DOCUMENTS

| | | |
|---|---|---|
| WO | WO 2017/187744 A1 | 11/2017 |
| WO | WO 2017/200070 A1 | 11/2017 |

OTHER PUBLICATIONS

International Search Report (Form PCT/ISA/210) for corresponding International Application No. PCT/JP2019/033145, dated Nov. 19, 2019, with English translation.
Yoneyama, "Introduction: Flow cytometric analysis of cell surface antigens (single color analysis, two color analysis)," Japanese Journal of Clinical Medicine, vol. 68, No. 6, 2010, pp. 843-846.
Japanese Office Action for corresponding Japanese Application No. 2020-538499, dated Jan. 11, 2022, with English translation.

\* cited by examiner

METHOD FOR DETECTING OBJECTIVE SUBSTANCE

CROSS-REFERENCE TO RELATED APPLICATIONS

This application is a Continuation of PCT International Application No. PCT/JP2019/033145 filed on Aug 23, 2019, which claims priority under 35 U.S.C. § 119(a) to Japanese Patent Application No. 2018-156617 filed on Aug. 23, 2018. The above application is hereby expressly incorporated by reference, in its entirety, into the present application.

BACKGROUND OF THE INVENTION

1. Field of the Invention

The present invention relates to a method for detecting an objective substance that is utilized in a case of detecting an objective substance such as a bacterium from an analyte.

2. Description of the Related Art

In the detection of minute organisms such as proteins, viruses and bacteria, it is preferable that an objective substance can be detected with high sensitivity even in a case where the objective substance is present in a small amount. In particular, it is important that viruses that may cause the spread of infectious diseases, such as influenza viruses and noroviruses, can be reliably detected even in a case where the amount of a virus in an analyte is very small.

As a highly sensitive detection method capable of detecting a small amount of a virus or the like, a polymerase chain reaction (PCR) is known.

In the polymerase chain reaction method, a virus or the like as a test object can be amplified about one million times in 20 cycles by amplifying only the base sequence that serves as a test object, by means of a polymerase chain reaction. Therefore, highly sensitive detection of viruses and the like is made possible.

On the other hand, the polymerase chain reaction method has problems that the influence of contaminants is large, the pretreatment is complicated, and refrigerated or frozen storage is required as in the case of a reagent test and the like.

In this regard, as a method capable of conveniently detecting a small amount of a virus or the like, there are known optical detection methods of forming a near field on a detection plate and detecting a conjugate including an objective substance (target substance) on the detection plate surface as an optical signal, as described in JP2017-219512A and WO2017/187744A.

In the optical detection methods described in JP2017-219512A and WO2017/187744A, for example, a conjugate in which magnetic particles and labeling particles (fluorescent particles or light scattering particles) are bound to an objective substance is produced by using an antigen-antibody reaction. On the other hand, a near field is generated on the front surface of the detection plate by the light irradiated from the back surface side under the conditions of total reflection. In this state, the conjugate thus produced is attracted to the near field (detection plate) by magnetic force and is caused to move in parallel with the detection plate. In the optical detection methods described in JP2017-219512A and WO2017/187744A, the objective substance is detected by measuring the fluctuation in the light amount, the movement of light (bright spot), and the like caused by this movement of the analyte.

SUMMARY OF THE INVENTION

In an optical detection method in which only labeling particles such as fluorescent particles are bound to an objective substance, there is a problem that non-specific adsorption causes adsorbed labeling particles other than the objective substance to become noise, which lowers the detection sensitivity, and highly sensitive detection of the objective substance cannot be carried out.

In contrast, in the methods described in JP2017-219512A and WO2017/187744A, non-specifically adsorbed labeling particles other than the objective substance are not moved by magnetic force, and only the conjugates of magnetic particles, the objective substance, and the labeling particles are moved by magnetic force while generating fluorescence or scattered light. Therefore, according to the method described in JP2017-219512A, noise caused by non-specifically adsorbed labeling particles can be removed, and an objective substance can be detected with high sensitivity, by detecting the movement of light (bright spot).

However, in the detection methods described in JP2017-219512A and WO2017/187744A, one kind of objective substance can be suitably detected; however, a plurality of kinds of objective substances cannot be detected.

An object of the present invention is to solve such a problem of conventional technologies and to provide a detection method for detecting an objective substance by causing magnetic particles and labeling particles to bind to the objective substance and causing a conjugate thereof to move by magnetic force, the method enabling detection of a plurality of kinds of objective substances.

In order to solve this problem, the present invention has the following configurations.

[1] A method for detecting an objective substance by causing magnetic particles and labeling particles to bind to the objective substance and causing a conjugate of the objective substance, magnetic particles, and labeling particles to move by magnetic force, the method comprising:

using a plurality of kinds of mutually different labeling particles capable of binding to one or more kinds of objective substances against a plurality of kinds of objective substances, the plurality of kinds of labeling particles including at least first labeling particles that bind to a first objective substance, and second labeling particles that bind to the first objective substance and are capable of binding to another objective substance to which the first labeling particles do not bind, and the plurality of kinds of labeling particles satisfying at least one of a first condition that the labeling particles have mutually different particle sizes, or a second condition that the labeling particles generate signal lights upon being irradiated with light and the signal lights are mutually different; and detecting the objective substance by a combination of labeling particles bound to the objective substance.

[2] The method for detecting an objective substance according to [1], wherein in a case where the plurality of kinds of labeling particles satisfy the first condition, between labeling particles having particle sizes that are closest to each other, the particle size of the larger labeling particle is two or more times the particle size of the smaller labeling particle.

[3] The method for detecting an objective substance according to [1] or [2], wherein in a case where the plurality of kinds of labeling particles satisfy the second condition, the labeling particles are particles that emit light upon being irradiated with light, and between labeling particles having emission wavelengths that are closest to each other, a difference in emission wavelength is 15 nm or more.

[4] The method for detecting an objective substance according to any one of [1] to [3], wherein the plurality of kinds of labeling particles satisfy both the first condition and the second condition.

[5] The method for detecting an objective substance according to any one of [1] to [4], wherein the detection of an objective substance is carried out by irradiation with light that causes labeling particles to generate the signal lights.

[6] The method for detecting an objective substance according to any one of [1] to [4], wherein the detection of the objective substance is carried out by enlarging a detection field of view for the objective substance and using observation light for observing a detection position of the objective substance.

[7] The method for detecting an objective substance according to any one of [1] to [6], wherein the detection of the objective substance is carried out while causing a conjugate to move by the magnetic force.

[8] The method for detecting an objective substance according to any one of [1] to [6], wherein the detection of the objective substance is carried out after causing the conjugate to move by the magnetic force.

[9] The method for detecting an objective substance according to any one of [1] to [8], wherein the first labeling particles are capable of binding to a third objective substance to which the second labeling particles do not bind.

[10] The method for detecting an objective substance according to any one of [1] to [9], wherein at least one party of the first labeling particles or the second labeling particles is modified with a plurality of antibodies, at least one party of the first labeling particles or the second labeling particles has at least one of a plurality of receptors or a plurality of ligands, bound thereto, or at least one party of the first labeling particles or the second labeling particles is modified with one or more antibodies and has at least one party of one or more receptors or one or more ligands, bound thereto.

[11] The method for detecting an objective substance according to any one of [1] to [10], wherein the plurality of kinds of labeling particles further include third labeling particles that do not bind to the first objective substance and are capable of binding to an objective substance to which the second labeling particles do not bind, and the second labeling particles are capable of binding to an objective substance other than the first objective substance, to which the third labeling particles do not bind.

[12] The method for detecting an objective substance according to [11], wherein at least one party of the first labeling particles, the second labeling particles, or the third labeling particles is capable of binding to one kind of an objective substance to which the other labeling particles are incapable of binding.

[13] The method for detecting an objective substance according to [11] or [12], wherein at least one party of the first labeling particles, the second labeling particles, or the third labeling particles are incapable of binding to one kind of an objective substance to which the other two parties of labeling particles are capable of binding.

[14] The method for detecting an objective substance according to any one of [11] to [13], wherein the first labeling particles, the second labeling particles, and the third labeling particles are capable of binding to one kind of the same objective substance.

According to the present invention, a plurality of kinds of objective substances can be detected in a detection method in which an objective substance is detected by causing magnetic particles and labeling particles to bind to the objective substance and causing a conjugate thereof to move by magnetic force.

DESCRIPTION OF THE PREFERRED EMBODIMENTS

Hereinafter, the method for detecting an objective substance according to embodiments of the present invention will be described in detail based on suitable Examples shown in the attached drawings.

In the present specification, the numerical value range represented using the term "to" means a range including the numerical values described before and after "to" as the lower limit value and the upper limit value.

The method for detecting an objective substance according to an embodiment of the present invention comprises forming a conjugate in which magnetic particles and labeling particles are bound to an objective substance, causing the conjugate to move by magnetic force, detecting the conjugate, that is, the labeling particles bound to the objective substance, and thereby detecting the objective substance.

Here, in the detection method according to the embodiment of the invention, a plurality of kinds of labeling particles are used.

The number of the plurality of kinds of labeling particles is not limited. Therefore, there may be two kinds of labeling particles, or three or more kinds of labeling particles. However, according to the present invention, the plurality of kinds of labeling particles essentially include at least first labeling particles that bind to at least a first objective substance, and second labeling particles that bind to the first objective substance and are capable of binding to another objective substance to which the first labeling particles do not bind.

Furthermore, the plurality of kinds of labeling particles satisfy at least one of a first condition or a second condition. The first condition is a condition that a plurality of kinds of labeling particles have mutually different particle sizes. The second condition is a condition that the labeling particles generate signal lights upon being irradiated with light, and for the plurality of labeling particles, the signal lights are mutually different.

The plurality of kinds of labeling particles may satisfy only the first condition, may satisfy only the second condition, or may satisfy both the first condition and the second condition. That is, the plurality of kinds of labeling particles may have only mutually different particle sizes, may only generate mutually different signal lights, or may have mutually different particle sizes and generate mutually different signal lights.

Figure 1:
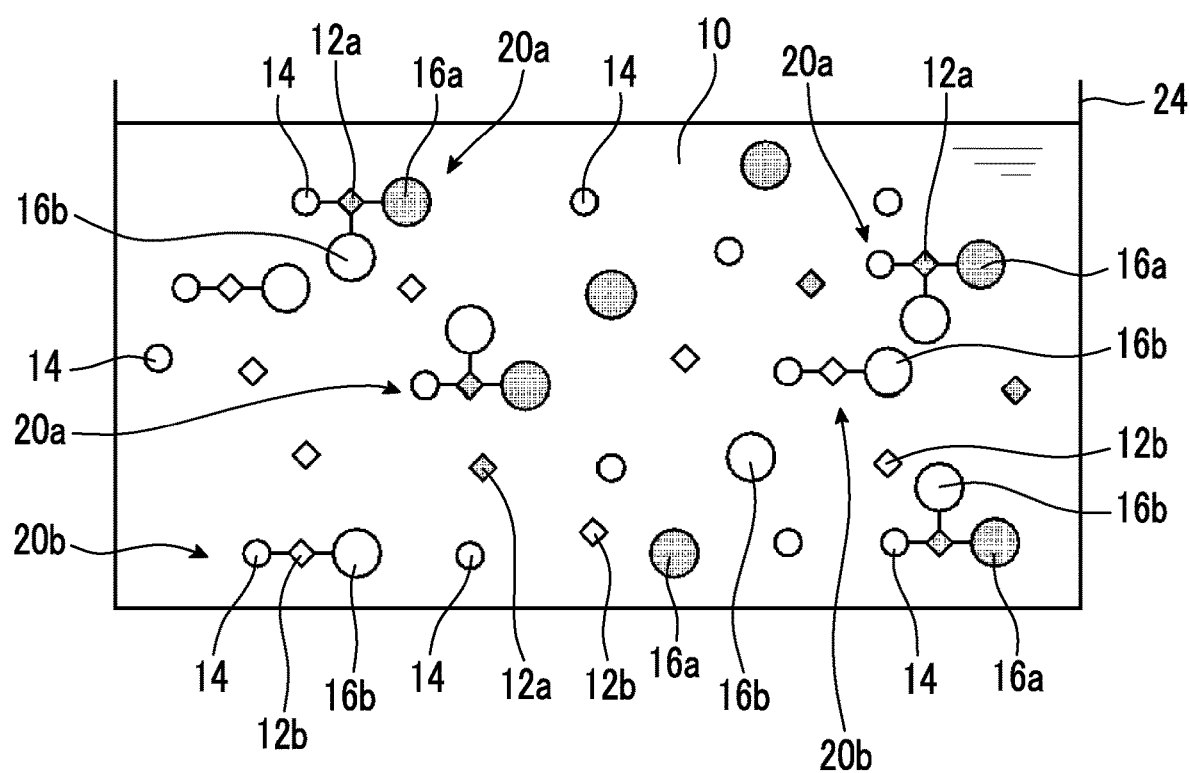
FIG. 1 is a conceptual diagram for explaining an example of a method for detecting an objective substance according to an embodiment of the present invention.

FIG. 1 conceptually shows a state in which an analyte is dissolved in a detection liquid 10 containing magnetic particles and labeling particles. According to the present invention, the phrase "dissolved in a detection liquid 10" includes not only a state in which a substance is dissolved in the detection liquid 10 but also a state in which a substance is dispersed in the detection liquid 10.

The detection liquid 10 is stored in a transparent cell 24. Magnetic particles 14, first labeling particles 16a, and second labeling particles 16b are dissolved in the detection liquid 10.

By dissolving an analyte in the detection liquid 10, for example, a first objective substance 12a and a second objective substance 12b are supplied to the detection liquid 10.

After an analyte is dissolved in the detection liquid 10, the solution may be left to stand for a predetermined time, may be stirred, may be left to stand for a predetermined time and then stirred, or may be stirred and then left to stand for a predetermined time.

The magnetic particles 14 specifically bind to the first objective substance 12a and the second objective substance 12b.

The first labeling particles 16a specifically bind to the first objective substance 12a. The second labeling particles 16b specifically bind to the first objective substance 12a and the second objective substance 12b. That is, in the example shown in FIG. 1, the first labeling particles 16a and the second labeling particles 16b bind to the first objective substance 12a, and only the second labeling particles 16b bind to the second objective substance 12b.

Therefore, by the dissolution of the analyte in the detection liquid 10, a conjugate 20a in which the first objective substance 12a, the magnetic particles 14, the first labeling particles 16a, and the second labeling particles 16b are bound together, and a conjugate 20b in which the second objective substance 12b, the magnetic particles 14, and the second labeling particles 16b are bound together, are formed.

Although not shown in the diagram, also present in the detection liquid 10 are a conjugate of the first objective substance 12a and the magnetic particles 14, a conjugate of the second objective substance 12b and the magnetic particles 14, a conjugate of the first objective substance 12a and the first labeling particles 16a, a conjugate of the first objective substance 12a and the second labeling particles 16b, a conjugate of the first objective substance 12a, the first labeling particles 16a and the second labeling particles 16b, a conjugate of the second objective substance 12b and the second labeling particles 16b, and the like.

Here, as described above, the first labeling particles 16a and the second labeling particles 16b satisfy at least one of a first condition that the labeling particles have mutually different particle sizes, or a second condition that the labeling particles are particles capable of generating signal lights upon being irradiated with light and the generated signal lights are mutually different.

The first labeling particles 16a and the second labeling particles 16b in the illustrated example are fluorescent particles that have the same particle size and emit fluorescence upon being irradiated with excitation light, and the emission wavelengths of the labeling particles are mutually different. As an example, the first labeling particles 16a emit red fluorescence upon being irradiated with excitation light, and the second labeling particles 16b emit blue fluorescence upon being irradiated with excitation light. That is, in the illustrated example, the first labeling particles 16a and the second labeling particles 16b satisfy only the second condition.

The method for detecting an objective substance according to the embodiment of the invention has such a configuration and thereby enables detection of a plurality of kinds of objective substances.

This point will be described later in detail.

According to the present invention, the objective substance (target substance) as a target of detection is not limited. Examples include viruses, bacteria, exosomes, DNA (deoxyribonucleic acid), RNA (ribonucleic acid), proteins, polysaccharides, and contaminants. Among them, viruses, proteins, and polysaccharides are suitable as the objective substance.

Further, there is no limitation on the analyte (sample to be collected) that is a target of detection for the objective substance, and various analytes that are considered to include the objective substance can be utilized. Examples of the analyte include body fluids such as blood and lymph, cells, endothelium (epithelial cells), saliva, sweat, nasal mucus, tears, vomitus, urine, feces, drugs, environmental water, tap water, sewage, and a wiping liquid.

These analytes may be collected by known methods in accordance with the analyte. Examples of the method for collecting an analyte include a method of wiping a doorknob, a table, and the like at a site where food poisoning has occurred, using a swab (cotton swab) or the like and thereby collecting an analyte. Another example of the method for collecting an analyte is a method of bringing a swab into contact with vomitus, urine, and the like and thereby collecting an analyte. Cells, endothelium, and the like may be collected using an endoscope or the like.

The magnetic particles (magnetic particles, a magnetic body, or a magnetic material) are also not limited, and various known magnetic particles that are used for the detection of an objective substance using magnetism can be utilized. For instance, magnetic beads, a magnetic powder, and the like are mentioned as examples. Commercially available products of these can also be utilized.

The labeling particles are also not limited, and various known particles can be utilized so long as the type of the particles can be identified by a method of utilizing a signal light generated by light irradiation, observation of a picked-up image or further image analysis, and magnified observation using a microscope, a magnifying optical system, and the like.

Suitable examples of the labeling particles include fluorescent particles that emit fluorescence upon being irradiated with excitation light, and light-scattering particles that scatter irradiated light and thereby generate scattered light.

There is no limitation on the fluorescent particles, and various kinds of known fluorescent particles that are used as labeling particles for the detection of an objective substance as described in the above-mentioned JP2017-219512A and WO2017/187744A can be utilized. Examples of the fluorescent particles include polymer particles containing fluorescent coloring agents, fluorescent pigments, rare earth elements and the like, silica particles, and silicon particles. Furthermore, quantum dots, biological fluorescent molecules, and the like can also be utilized. Among these, suitable examples include polymer particles containing fluorescent coloring agents, quantum dots, fluorescent pigments, rare earth elements and the like, fluorescent pigments, and biological fluorescent molecules. Commercially available products of these can also be utilized. Further, the labeling particles may also be phosphorescent particles.

In a case where fluorescent particles are used as the labeling particles, the plurality of labeling particles may be particles that have the same particle size and satisfy only the second condition that the wavelengths of the generated signal lights, that is, the emission wavelengths (fluorescence wavelengths) are mutually different; may be particles that have the same emission wavelength and satisfy only the first condition that the particle sizes are mutually different; or may be particles that satisfy both the first condition and the second condition.

The light-scattering particles are also not limited, and similarly, various kinds of known light-scattering particles that are used as labeling particles for the detection of an objective substance as described in the above-mentioned JP2017-219512A and WO2017-187744A can be utilized. Examples of the light-scattering particles include polystyrene beads, metal particles such as gold particles, and silicon particles. Commercially available products of these can also be utilized.

In a case where light-scattering particles are used as the labeling particles, it is preferable that the plurality of kinds of labeling particles satisfy the first condition that the labeling particles have mutually different particle sizes.

Depending on the type of the objective substance, the objective substance may generate fluorescence upon being irradiated with excitation light. At this time, the objective substance may also serve as the labeling particles.

Furthermore, depending on the type of the labeling particles, the labeling particles may be magnetic. In this case, the labeling particles may also serve as the magnetic particles (the magnetic particles may serve as the labeling particles).

There is no limitation also on the method of causing the objective substance to bind to the magnetic particles and the method of causing the objective substance to bind to the labeling particles, and any known method can be utilized depending on the types of the objective substance and the magnetic particles, and on the types of the objective substance and the labeling particles. Examples include physical adsorption, an antigen-antibody reaction, binding between a receptor and a ligand, DNA hybridization, chelate bonding, and amino bonding.

Physical adsorption is a method of causing an objective substance to bind magnetic particles by utilizing electrostatic binding force such as hydrogen bonding. Physical adsorption can be easily carried out because treatment of magnetic particles and the like are unnecessary. On the other hand, in the physical adsorption, the selectivity is low because magnetic particles and labeling particles do not specifically adsorb to the objective substance. That is, in the physical adsorption, there is a possibility that the magnetic particles and the labeling particles may bind to a substance other than the objective substance included in an analyte.

In contrast, the antigen-antibody reaction, the reaction between a receptor and a ligand, and the like utilize specific binding to the objective substance, and therefore, there is an advantage that the magnetic particles and the labeling particles can be selectively caused to bind to the objective substance.

At the time of utilizing the antigen-antibody reaction, in a case where the objective substance is, for example, an antigen such as a bacterium, a virus, or an exosome, at least one of the magnetic particles or the labeling particles is required to be modified with an antibody against the objective substance in advance so as to prepare antibody-modified magnetic particles, antibody-modified labeling particles, and the like. Furthermore, in a case where the objective substance is a bacterium, a virus, an exosome, or the like itself, it is necessary to cause an antibody against an antigen that is present on the surface and the like of these objective substances to bind in advance to at least one of the magnetic particles or the labeling particles.

Furthermore, in the case of utilizing the binding between a receptor and a ligand, it is necessary to cause a receptor or a ligand, which specifically binds to the objective substance, to bind in advance to at least one of the magnetic particles or the labeling particles. Furthermore, in a case where the objective substance is a bacterium, a virus, an exosome or the like itself, it is necessary to cause in advance a ligand for a receptor that is present on the surface or the like of these objective substances, or a receptor for a ligand that is present on the surface or the like of these objective substances, to bind to at least one of the magnetic particles or the labeling particles.

In a case where both the magnetic particles and the labeling particles are caused to bind to the objective substance, it is preferable that at least one party of the binding is binding specific to the objective substance, such as an antigen-antibody reaction or binding between a receptor and a ligand.

In a case where both the magnetic particles and the labeling particles are caused to bind to the objective substance, in a case where the binding is non-specific binding for both parties, both the magnetic particles and the labeling particles bind to foreign materials other than the objective substance. In this case, there occurs inconvenience that the objective substance and the foreign materials become undistinguishable.

As described above, according to the present invention, magnetic particles that generate signal light upon being irradiated with light (magnetized labeling particles), such as magnetic particles that generate fluorescence upon being irradiated with excitation light, can also be utilized.

In this case, it is preferable that the binding between magnetic particles that emit fluorescence upon being irradiated with excitation light and the objective substance and particles is specific binding to the objective substance, such as an antigen-antibody reaction. In a case where the binding between magnetic particles that emit fluorescence upon being irradiated with excitation light and the objective substance is non-specific binding, the magnetic particles that emit fluorescence upon being irradiated with excitation light may bind to foreign materials other than the objective substance. In this case, there occurs inconvenience that the objective substance and the foreign materials become undistinguishable.

According to the present invention, various liquids capable of dissolving the analyte, the magnetic particles, and the objective substance can be utilized as the detection liquid 10. Specifically, examples of the detection liquid 10 include a phosphate buffer solution, a Tris buffer solution, an acetate buffer solution, a citrate buffer solution, a tartrate buffer solution, PBS (phosphate buffered saline), water, and water-based liquids. Regarding water, it is preferable to use any of pure water, ion-exchanged water, or distilled water.

Hereinafter, the method for detecting an objective substance according to embodiments of the present invention will be described in more detail with reference to FIG. 1 and FIG. 2.

As described above, in the example shown in FIG. 1, magnetic particles 14, first labeling particles 16a, and second labeling particles 16b are dissolved in a detection liquid 10 stored in a transparent cell 24. The first labeling particles 16a and the second labeling particles 16b are both fluorescent particles, and upon being irradiated with excitation light, the first labeling particles 16a emit red fluorescence while the second labeling particles 16b emit blue fluorescence, as described above.

By dissolving an analyte in this detection liquid 10, the first objective substance 12a and the second objective substance 12b are supplied to the detection liquid 10.

In the method for detecting an objective substance according to the embodiment of the invention, the analyte may be first dissolved in the detection liquid, and then the magnetic particles and the labeling particles may be dissolved (dispersed) in the detection liquid simultaneously or sequentially.

That is, in the method for detecting an objective substance according to the embodiment of the invention, there is no limitation on the order of dissolution (order of supply) of the analyte (objective substance), the magnetic particles, and the labeling particles in the detection liquid.

By dissolving the analyte in the detection liquid 10 and supplying the first objective substance 12a, the second objective substance 12b, and the magnetic particles 14, a conjugate 20a in which the first objective substance 12a, the magnetic particles 14, the first labeling particles 16a, and the second labeling particles 16b are bound together, and a conjugate 20b in which the second objective substance 12b, the magnetic particles 14, and the second labeling particles 16b are bound together, are formed.

Although not shown in the diagram, it is as described above that a conjugate of the magnetic particles and the objective substance, a conjugate of the labeling particles and the objective substance, and the like are formed in the detection liquid 10.

Figure 2:
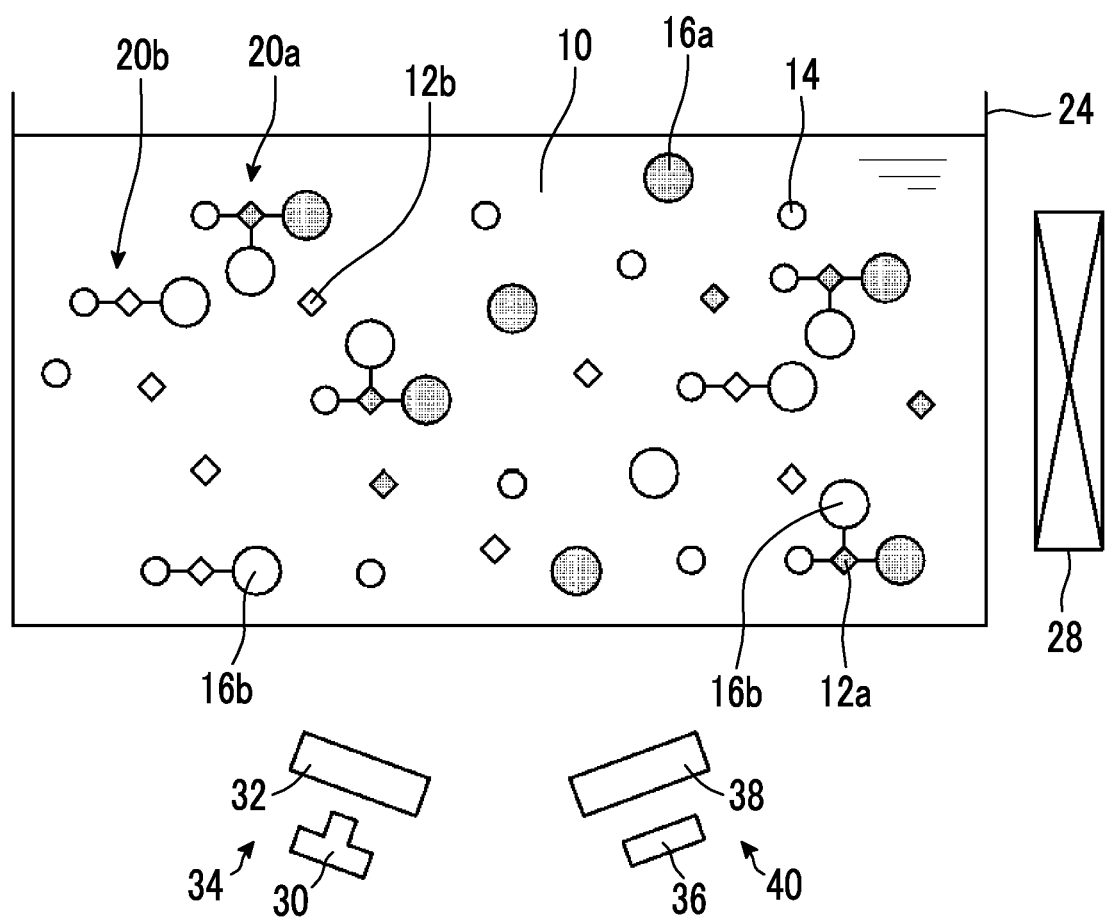
FIG. 2 is a conceptual diagram for explaining the method for detecting an objective substance shown in FIG. 1.

As an example, a magnet 28 is disposed on the right-hand side of the cell 24 in the drawing, as conceptually shown in FIG. 2. The magnet 28 is a known magnet.

Furthermore, an excitation light irradiation unit 34 having a light source 30 and a light condensing optical system 32 is provided such that the interior of the cell 24 is irradiated with the excitation light through the bottom face of the cell 24. An image pick-up unit 40 having an imaging element 36 and a light condensing optical system 38 is provided so as to capture an image of an region irradiated with excitation light by the excitation light irradiation unit 34 inside the cell 24 through the bottom face of the cell 24.

It is preferable that the position of image pick-up (focus of imaging) by the image pick-up unit 40 is not on the wall surface (near field) of the cell 24 but inside the cell 24.

Regarding the light source 30, various light sources capable of performing irradiation with light that excites the first labeling particles 16a and the second labeling particles 16b and emits fluorescence can be utilized. For instance, examples include a light bulb such as a mercury lamp, a fluorescent lamp, a halogen lamp, a Light Emitting Diode (LED), and a laser such as a semiconductor laser.

Also regarding the imaging element 36, various imaging elements capable of measuring the fluorescence emitted by the first labeling particles 16a and the second labeling particles 16b can be utilized. For instance, examples include a Complementary Metal Oxide Semiconductor (CMOS) image sensor (CMOS camera) and a Charge-Coupled Device (CCD) image sensor (CCD camera).

The light condensing optical systems are both known light condensing optical systems.

The light source 30 may be provided with an optical filter such as a bandpass filter, as necessary. Furthermore, the imaging element 36 and/or the light condensing optical system 38 may be provided with an optical filter such as a sharp cutoff filter, as necessary.

The method for detecting an objective substance according to the embodiment of the invention is not limited to a configuration using such an optical system that performs irradiation with excitation light and an optical system that performs image pick-up, and various methods can be utilized so long as the interior of the cell 24 can be observed while the labeling particles in the cell 24 can be caused to generate fluorescence.

For example, in a case where the interior of the cell 24 can be observed with a fluorescence microscope, detection of the objective substance may be carried out by observing the interior of the cell 24 using a fluorescence microscope. At this time, a microscopic image obtained using a fluorescence microscope may be picked up with a CCD image sensor or the like, as necessary.

Furthermore, in the method for detecting an objective substance according to the embodiment of the invention, there is no limitation on the configuration of picking up an image of the interior of the cell 24 using an image pick-up unit 40, and detection of the objective substance may be carried out by observing the movement of the conjugate (labeling particles) that will be described below, by visual observation.

The interior of the cell 24 is irradiated with excitation light by the excitation light irradiation unit 34, and the magnet 28 is actuated while the excitation light-irradiated region inside the cell 24 is imaged by the image pick-up unit 40.

Upon being irradiated with the excitation light, the first labeling particles 16a emit red fluorescence, and the second labeling particles 16b emit blue fluorescence.

Furthermore, by the magnetic force of the magnet 28; the magnetic particles 14, the conjugate 20a in which the first objective substance 12a, the magnetic particles 14, the first labeling particles 16a, and the second labeling particles 16b are bound together; and the conjugate 20b in which the second objective substance 12b, the magnetic particles 14, and the second labeling particles 16b are bound together, move toward the magnet 28 due to the magnetic force.

Here, the first labeling particles 16a and the second labeling particles 16b emit fluorescence upon being irradiated with excitation light; however, these labeling particles do not move by magnetic force because they do not have magnetic particles. In this regard, the same also applies to the conjugate of the objective substance and the labeling particles.

On the other hand, the magnetic particles 14 move due to the magnetic force; however, the magnetic particles do not emit fluorescence because they do not have labeling particles. In this regard, the same also applies to the conjugate of the objective substance and the magnetic particles.

That is, only in a case where at least one of the first objective substance 12a or the second objective substance 12b is present in the detection liquid 10, a conjugate of the objective substance, the magnetic particles, and the labeling particles is formed, and fluorescence (luminous body) moves toward the magnet 28 due to the irradiation of excitation light and the magnetic force of the magnet 28.

Specifically, in a case where only the first objective substance 12a is included in the detection liquid 10, that is, the analyte, only the conjugate 20a in which the first objective substance 12a, the magnetic particles 14, the first labeling particles 16a, and the second labeling particles 16b are bound together is formed, and the conjugate 20b in which the second objective substance 12b, the magnetic particles 14, and the second labeling particles 16b are bound together is not formed.

Therefore, in this case, red fluorescence and blue fluorescence are generated by the irradiation of excitation light; however, in a case where the magnet 28 is actuated, the single blue fluorescence does not move, and only the fluorescence resulting from integration of the red fluorescence and the blue fluorescence moves toward the magnet 28.

In a case where only the second objective substance 12b is included in the detection liquid 10, that is, the analyte, only the conjugate 20b in which the second objective substance 12b, the magnetic particles 14, and the second labeling particles 16b are bound together is formed, and the conjugate 20a in which the first objective substance 12a, the magnetic particles 14, the first labeling particles 16a, and the second labeling particles 16b are bound together is not formed.

Therefore, in this case, red fluorescence and blue fluorescence are generated by the irradiation of excitation light; however, in a case where the magnet 28 is actuated, only the single blue fluorescence moves toward the magnet 28.

In a case where both the first objective substance 12a and the second objective substance 12b are included in the detection liquid 10, that is, the analyte, the conjugate 20a in which the first objective substance 12a, the magnetic particles 14, the first labeling particles 16a, and the second labeling particles 16b are bound together; and the conjugate 20b in which the second objective substance 12b, the magnetic particles 14, and the second labeling particles 16b are bound together, are formed.

Therefore, in this case, red fluorescence and blue fluorescence are generated by the irradiation of excitation light, and in a case where the magnet 28 is actuated, fluorescence resulting from integration of the red fluorescence and the blue fluorescence, and the single blue fluorescence moves toward the magnet 28.

Furthermore, in a case where neither the first objective substance 12a nor the second objective substance 12b is included in the analyte, the conjugate 20a and the conjugate 20b are not formed. Therefore, in this case, red fluorescence and blue fluorescence are generated by the irradiation of excitation light; however, there is no moving fluorescence even though the magnet 28 is actuated.

Therefore, whether the first objective substance 12a and the second objective substance 12b are present in an analyte can be detected by analyzing images that have been picked up by the imaging element 36, detecting the movement of the fluorescence resulting from integration of red fluorescence and blue fluorescence and the movement of blue fluorescence, or further counting the fluorescence.

That is, according to the present invention in which a plurality of kinds of labeling particles that emit mutually different fluorescence are used, and the plurality of kinds of labeling particles include at least first labeling particles that bind to a first objective substance, and second labeling particles that bind to the first objective substance and are capable of binding to another objective substance to which the first labeling particles do not bind, a plurality of kinds of objective substances can be detected by the combination of the labeling particles bound to the objective substances.

The above example is an example in which the excitation light irradiated from the light source 30 excites both the first labeling particles 16a and the second labeling particles 16b to emit fluorescence. However, in some cases, one kind of excitation light cannot excite both the first labeling particles 16a and the second labeling particles 16b.

In this case, it is desirable that a first excitation light irradiation unit that excites the first labeling particles 16a to emit fluorescence, and a second excitation light irradiation unit that excites the second labeling particles 16b to emit fluorescence are provided, the two excitation light irradiation unit are simultaneously driven, thereby detection of the conjugate 20a having the first labeling particles 16a is conducted similarly to the example described above, or first using the first excitation light irradiation unit, and then the conjugate 20b having the second labeling particles 16b is detected using the second excitation light irradiation unit, or counting is further performed.

Alternatively, it is also acceptable that a light source capable of performing irradiation with broadband light, such as a halogen lamp, a first filter that transmits light which excites the first labeling particles 16a to emit fluorescence, and a second filter that transmits light which excites the second labeling particles 16b to emit fluorescence are used, the first filter, for example, is first inserted into the optical path, thereby detection of the conjugate 20a having the first labeling particles 16a is carried out, subsequently the second filter is inserted into the optical path, and thereby the conjugate 20b having the second labeling particles 16b is detected, or counting is further performed.

It is also acceptable that a light source capable of irradiating broadband light, such as a halogen lamp, or a plurality of light sources capable of exciting the various labeling particles, and a plurality of light receiving elements for receiving a variety of fluorescence wavelengths are disposed, and fluorescence corresponding to each of the conjugates is detected with a corresponding light receiving element, or counting is further performed.

In the method for detecting an objective substance according to the embodiment of the invention, various methods can be utilized for the movement and detection of the conjugate 20a and the conjugate 20b by magnetic force.

Figure 3:
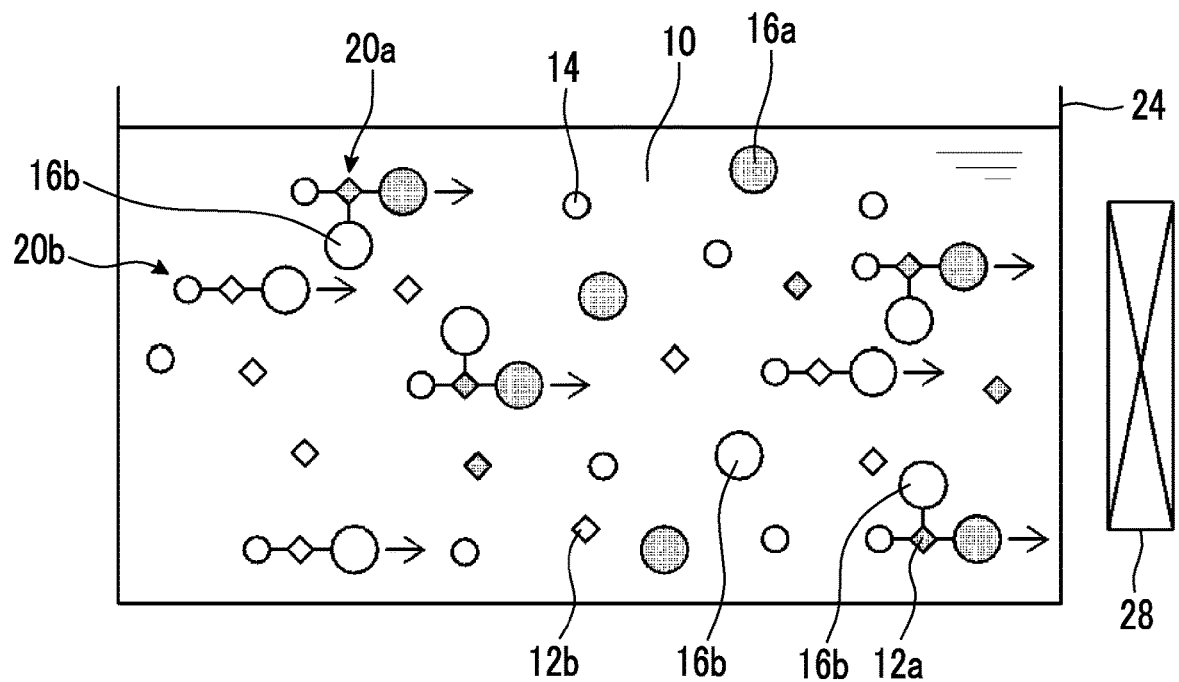
FIG. 3 is a conceptual diagram for explaining an example of the method for detecting an objective substance according to an embodiment of the present invention.

For example, as conceptually shown in FIG. 3, one magnet 28 is disposed, the interior of the cell 24 is irradiated with excitation light, the conjugate 20a and the conjugate 20b are moved in one direction by the magnetic force of the magnet 28 while image pick-up is performed in the region irradiated with the excitation light, and detection of fluorescence moving toward the magnet 28 in the picked-up image or further counting is performed. Thereby, detection of the first objective substance 12a and the second objective substance 12b may be carried out. This method can be utilized in a configuration having a plurality of magnets.

Figure 4:
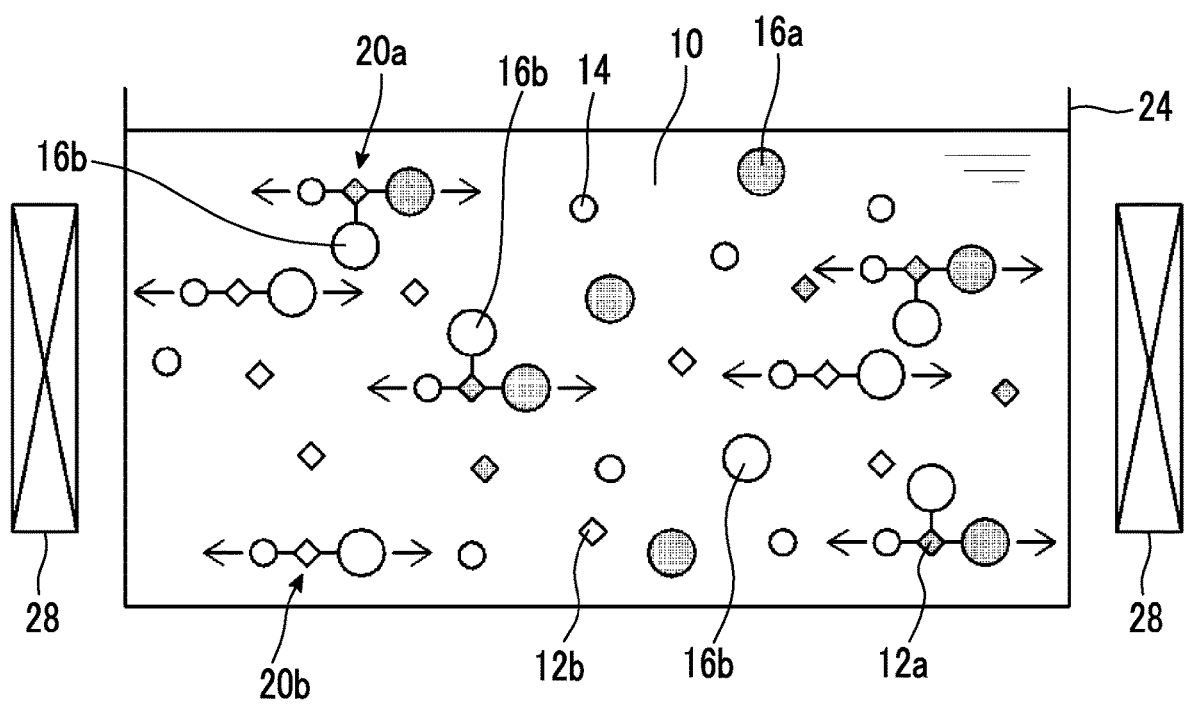
FIG. 4 is a conceptual diagram for explaining another example of the method for detecting an objective substance according to the embodiment of the present invention.

In addition, as conceptually shown in FIG. 4, detection of the first objective substance 12a and the second objective substance 12b may also be carried out by disposing two magnets 28 so as to interpose the cell 24 therebetween, irradiating the interior of the cell 24 with excitation light, alternately actuating the two magnets while performing image pick-up in the region irradiated with the excitation light, thereby causing the conjugate 20a and the conjugate 20b to reciprocatingly move by magnetic force, and thereby performing detection of fluorescence that reciprocatingly move in the picked-up image, or performing further counting. Alternatively, it is also acceptable that magnets are also disposed above and below the cell 24 in the diagram, the interior of the cell 24 is irradiated with excitation light, the respective magnets are actuated while image pick-up is performed in the region irradiated with the excitation light, the conjugate 20a and the conjugate 20b are caused to move two-dimensionally (rectangular-shaped) by magnetic force, and that thereby detection of the first objective substance 12a and the second objective substance 12b is carried out.

Figure 5:
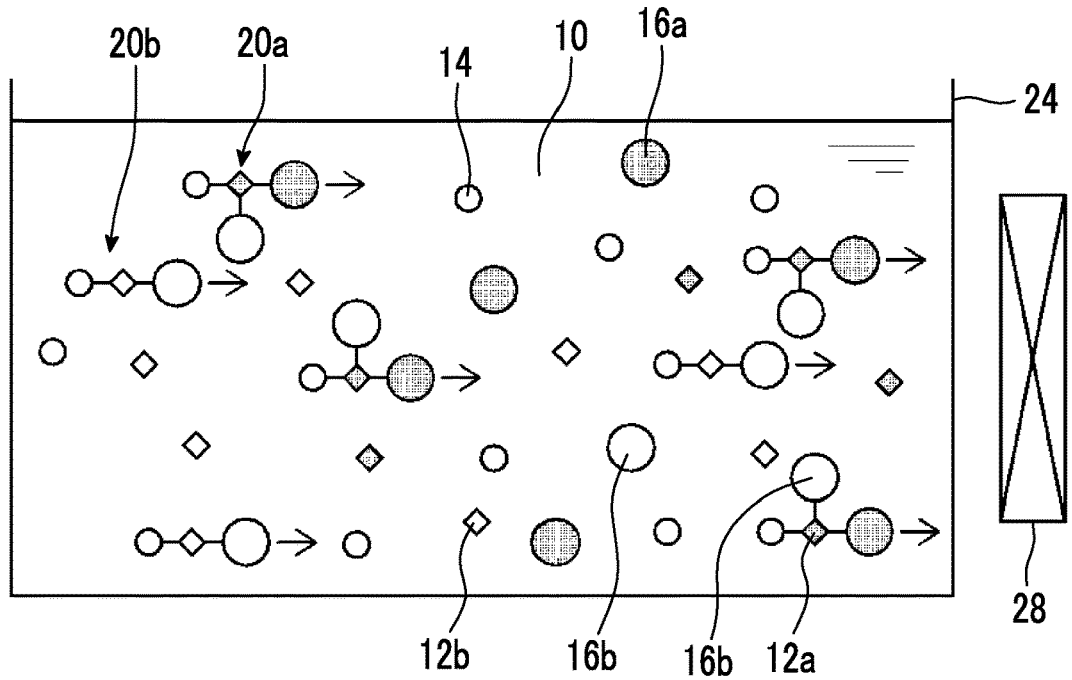
FIG. 5 is a conceptual diagram for explaining another example of the method for detecting an objective substance according to the embodiment of the present invention.
Figure 5:
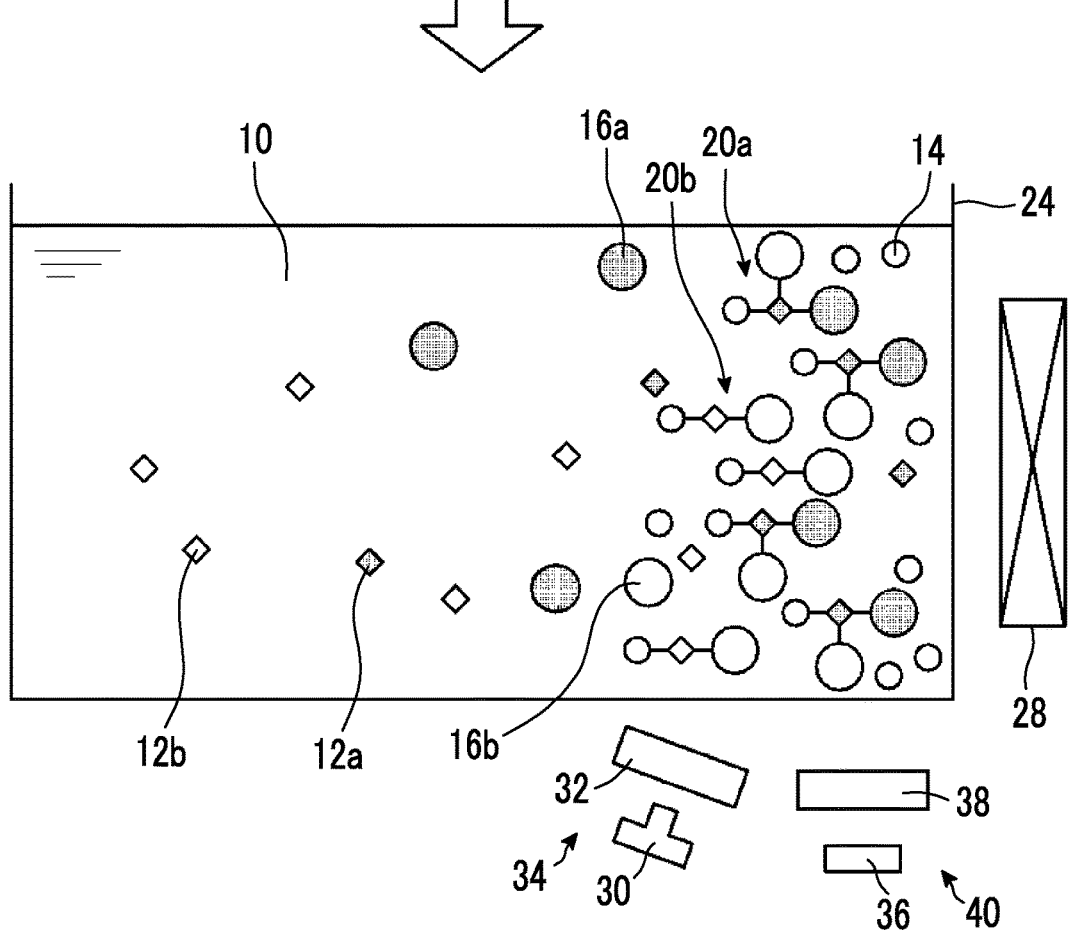

Furthermore, as conceptually shown in FIG. 5, one magnet 28 is disposed, the magnet 28 is first actuated, and thereby the conjugate 20a and the conjugate 20b are gathered on the magnet 28 side in the cell 24 by magnetic force. Subsequently, detection of the first objective substance 12a and the second objective substance 12b may be carried out by irradiating the region where the conjugate 20a and the conjugate 20b have been gathered in the cell 24 with excitation light without actuating the magnet 28 as necessary, performing image pick-up of the region irradiated with the excitation light, and performing detection of fluorescence located on the magnet 28 side in the picked-up image, or performing further counting. This method can also be utilized in a configuration having a plurality of magnets.

In the method of detecting an objective substance in the illustrated example, the first labeling particles 16a and the second labeling particles 16b have mutually different signal lights generated upon being irradiated with light. Specifically, the first labeling particles 16a and the second labeling particles 16b emit fluorescence upon being irradiated with excitation light and have mutually different emission wavelengths, such that the first labeling particles 16a emit red fluorescence while the second labeling particles 16b emit blue fluorescence.

As such, the plurality of kinds of labeling particles are particles that emit light upon being irradiated with light such as excitation light, and there is no limitation on the difference in the emission wavelength in a case where the second condition according to the invention is satisfied. In a case where the plurality of kinds of labeling particles satisfy the second condition according to the invention, the difference in the emission wavelength between labeling particles having the closest emission wavelengths is preferably 15 nm or more, more preferably 25 nm or more, and even more preferably 50 nm or more.

By setting the difference in the emission wavelength to 15 nm or more, it becomes possible to more suitably carry out the identification of a plurality of kinds of labeling particles that bind to the objective substances and move, and thus the detection of a plurality of kinds of objective substances can be easily carried out with higher accuracy.

The examples shown in FIG. 1 and FIG. 2 involves detection of two kinds of objective substances by using two kinds of labeling particles; however, the present invention is not limited to this.

For example, in the method for detecting an objective substance according to the embodiment of the invention, it is also possible to similarly perform the detection of three kinds of objective substances using two kinds of labeling particles.

As described above, in the method for detecting an objective substance according to the embodiment of the invention, the first labeling particles 16a bind to at least the first objective substance 12a. On the other hand, the second labeling particles 16b bind to the first objective substance 12a and are capable of binding to another objective substance to which the first labeling particles 16a do not bind, and in the examples shown in FIG. 1 and FIG. 2, the second labeling particles 16b are capable of binding to the second objective substance 12b.

In contrast, in the case of performing the detection of a third objective substance 12c in addition to the first objective substance 12a and the second objective substance 12b, the first labeling particles 16a are made capable of binding also to the third objective substance 12c in addition to the first objective substance 12a.

That is, the first labeling particles 16a specifically bind to the first objective substance 12a and the third objective substance 12c, and the second labeling particles 16b specifically bind to the first objective substance 12a and the second objective substance.

Also in this example, it is assumed that the magnetic particles 14 specifically bind to all of the objective substances.

That is, according to the present invention, for example, in a case where the objective substance is detected by utilizing an antigen-antibody reaction and in a case where the objective substance is detected by utilizing binding between a receptor and a ligand, the first labeling particles 16a and/or the second labeling particles 16b may be modified with a plurality of antibodies or may have a plurality of receptors and/or ligands bound thereto, or the first labeling particles 16a and/or the second labeling particles 16b may be modified with one or more antibodies and have one or more receptors and/or ligands bound thereto.

In this regard, the same applies to the third labeling particles 16c that will be described later, and also to the other labeling particles that are used as necessary.

Figure 6:
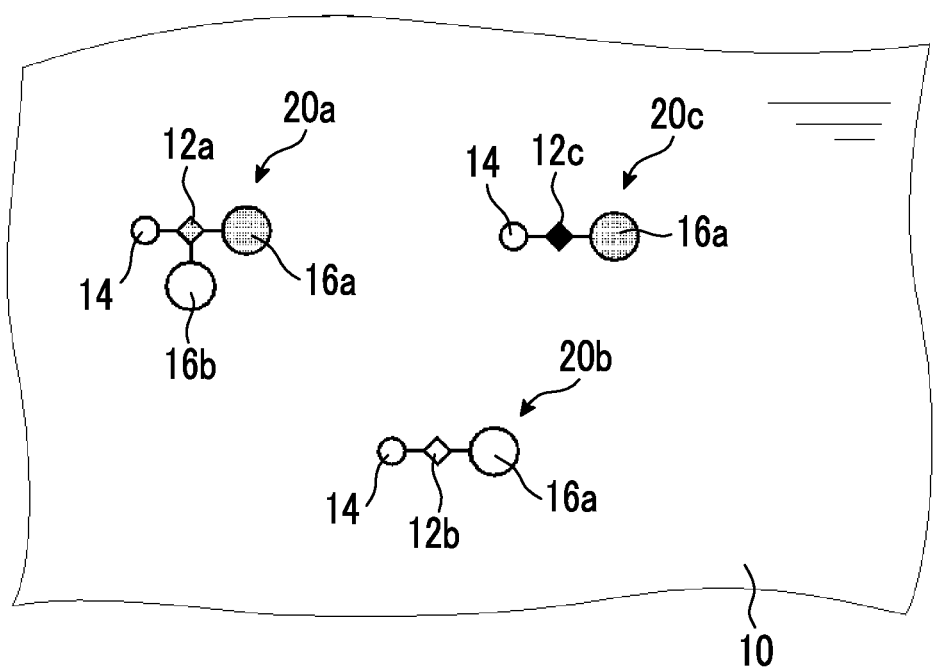
FIG. 6 is a conceptual diagram for explaining another example of the method for detecting an objective substance according to the embodiment of the present invention.

According to this configuration, as conceptually shown in FIG. 6, in a case where the first objective substance 12a is present in the detection liquid 10, that is, the analyte, the conjugate 20a of the first objective substance 12a, the magnetic particles 14, the first labeling particles 16a, and the second labeling particles 16b is formed as in the case of the above-mentioned example.

Therefore, in a case where the first objective substance 12a is present in the detection liquid 10, fluorescence resulting from integration of red fluorescence and blue fluorescence moves toward the magnet 28 due to the irradiation of excitation light and the magnetic force of the magnet 28, as in the case of the above-mentioned example. Furthermore, in a case where the first objective substance 12a is not present in the detection liquid 10, since the conjugate 20a is not formed, there is no fluorescence resulting from integration of red fluorescence and blue fluorescence, which moves toward the magnet 28.

In a case where the second objective substance 12b is present in the detection liquid 10, the conjugate 20b of the second objective substance 12b, the magnetic particles 14, and the second labeling particles 16b is formed as in the case of the above-mentioned example.

Therefore, in a case where the second objective substance 12 is present in the detection liquid 10, single blue fluorescence moves toward the magnet 28 due to the irradiation of excitation light and the magnetic force of the magnet 28, as in the case of the above-mentioned example. Furthermore, in a case where the second objective substance 12b is not present in the detection liquid 10, since the conjugate 20b is not formed, there is no single blue fluorescence that moves toward the magnet 28.

In a case where the third objective substance 12c is present in the detection liquid 10, a conjugate 20c of the third objective substance 12c, the magnetic particles 14, and the first labeling particles 16a is formed, which does not exist in the above-mentioned example.

Therefore, in a case where the third objective substance 12c is present in the detection liquid 10, single red fluorescence caused by the conjugate 20c moves toward the magnet 28, which does not exist in the above-mentioned example, due to the irradiation of excitation light and the magnetic force of the magnet 28. Furthermore, in a case where the third objective substance 12c is not present in the detection liquid 10, since the conjugate 20c is not formed, there is no single red fluorescence moving toward the magnet 28.

That is, by detecting such movement of fluorescence, as in the case of the above-mentioned example, detection of the first objective substance 12a, the second objective substance 12b, and the third objective substance 12c, which are present in the detection liquid 10, that is, the analyte, is enabled by a single detection by a combination of moving fluorescence, that is, a combination of labeling particles bound to the objective substances.

Furthermore, according to the present invention, it is possible to detect a larger number of kinds of objective substances by a single detection, by increasing the number of labeling particles.

As described above, in the method for detecting an objective substance according to the embodiment of the present invention, the first labeling particles 16a are particles that bind to at least the first objective substance 12a, and the second labeling particles 16b are particles that bind to the first objective substance 12a and are capable of binding to another objective substance to which the first labeling particles 16a do not bind.

Figure 7:
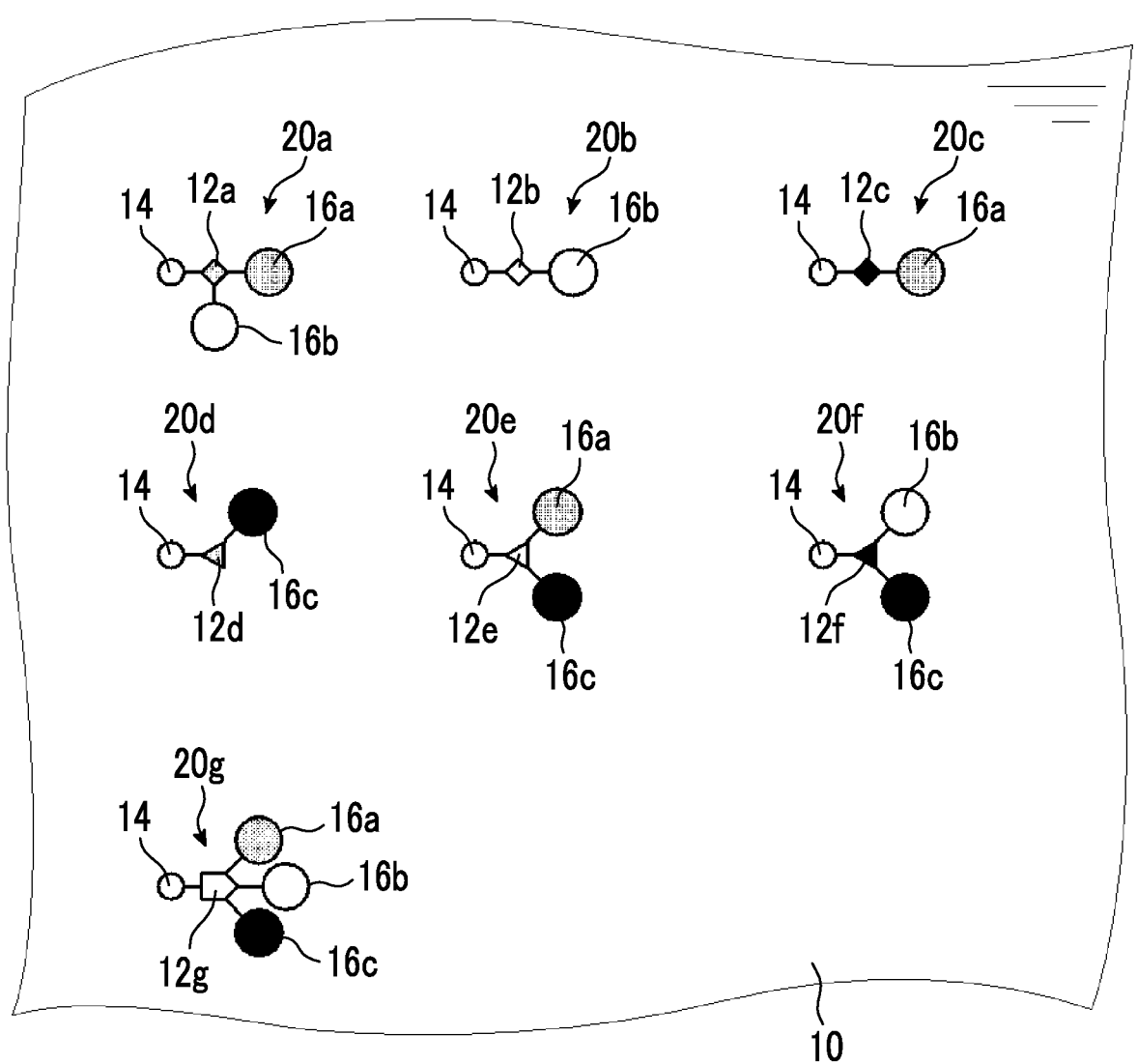
FIG. 7 is a conceptual diagram for explaining another example of the method for detecting an objective substance according to the embodiment of the present invention.

For example, in addition to this, as conceptually shown in FIG. 7, third labeling particles 16c that do not bind to the first objective substance 12a and are capable of binding to an objective substance to which the second labeling particles 16b do not bind, are used.

Specifically, in the example shown in FIG. 7, third labeling particles 16c that emit green fluorescence are used in addition to the above-described first labeling particles 16a that emit red fluorescence and the second labeling particles 16b that emit blue fluorescence.

In this example, seven kinds of objective substances, namely, the first objective substance 12a to the seventh objective substance 12g, are detected using these three kinds of labeling particles.

The first labeling particles 16a specifically bind to the fifth objective substance 12e and the seventh objective substance 12g, in addition to the above-described first objective substance 12a and third objective substance 12c.

The second labeling particles 16b specifically bind to the sixth objective substance 12f and the seventh objective substance 12g, in addition to the above-described first objective substance 12a and second objective substance 12b.

Furthermore, the third labeling particles 16c specifically bind to the fourth objective substance 12d, the fifth objective substance 12e, the sixth objective substance 12f, and the seventh objective substance 12g.

Also in this example, it is assumed that the magnetic particles 14 specifically bind to all of the objective substances.

Therefore, in the example shown in FIG. 7, in a case where the first objective substance 12a is present in the detection liquid 10, that is, the analyte, the conjugate 20a of the first objective substance 12a, the magnetic particles 14, the first labeling particles 16a, and the second labeling particles 16b is formed as in the case of the above-mentioned example.

As a result, in a case where the first objective substance 12a is present in the detection liquid 10, that is, the analyte, fluorescence resulting from integration of red fluorescence and blue fluorescence moves toward the magnet 28 due to the irradiation of excitation light and the magnetic force of the magnet 28, as in the case of the above-mentioned example. Furthermore, in a case where the first objective substance 12a is not present in the detection liquid 10, since the conjugate 20a is not formed, there is no fluorescence resulting from integration of red fluorescence and blue fluorescence, which moves toward the magnet 28.

In a case where the second objective substance 12b is present in the detection liquid 10, the conjugate 20b of the second objective substance 12b, the magnetic particles 14, and the second labeling particles 16b is formed as in the case of the above-mentioned example.

As a result, in a case where the second objective substance 12b is present in the detection liquid 10, single blue fluorescence moves toward the magnet 28 due to the irradiation of excitation light and the magnetic force of the magnet 28 as in the case of the above-mentioned example. Furthermore, in a case where the second objective substance 12b is not present in the detection liquid 10, since the conjugate 20b is not formed, there is no single blue fluorescence moving toward the magnet 28.

In a case where the third objective substance 12c is present in the detection liquid 10, the conjugate 20c of the third objective substance 12c, the magnetic particles 14, and the first labeling particles 16a is formed as in the case of the above-mentioned example.

As a result, in a case where the third objective substance 12c is present in the detection liquid 10, single red fluorescence moves toward the magnet 28 due to the irradiation of excitation light and the magnetic force of the magnet 28, as in the case of the above-mentioned example. Furthermore, in a case where the third objective substance 12c is not present in the detection liquid 10, since the conjugate 20c is not formed, there is no single red fluorescence moving toward the magnet 28.

In a case where a fourth objective substance 12d is present in the detection liquid 10, a conjugate 20d of the fourth objective substance 12d, the magnetic particles 14, and the third labeling particles 16c is formed.

As a result, in a case where the fourth objective substance 12d is present in the detection liquid 10, single green fluorescence moves toward the magnet 28 due to the irradiation of excitation light and the magnetic force of the magnet 28. Furthermore, in a case where the fourth objective substance 12d is not present in the detection liquid 10, since the conjugate 20d is not formed, there is no single green fluorescence moving toward the magnet 28.

In a case where a fifth objective substance 12e is present in the detection liquid 10, a conjugate 20e of the fifth objective substance 12e, the magnetic particles 14, the first labeling particles 16a, and the third labeling particles 16c is formed.

As a result, in a case where the fifth objective substance 12e is present in the detection liquid 10, fluorescence resulting from integration of red fluorescence and green fluorescence moves toward the magnet 28 due to the irradiation of excitation light and the magnetic force of the magnet 28. Furthermore, in a case where the fifth objective substance 12e is not present in the detection liquid 10, since the conjugate 20e is not formed, there is no fluorescence resulting from integration of red fluorescence and green fluorescence moving toward the magnet 28.

In a case where a sixth objective substance 12*f* is present in the detection liquid 10, a conjugate 20*f* of the sixth objective substance 12*f*, the magnetic particles 14, the second labeling particles 16*b*, and the third labeling particles 16*c* Is formed.

As a result, in a case where the sixth objective substance 12*f* is present in the detection liquid 10, fluorescence resulting from integration of blue fluorescence and green fluorescence moves toward the magnet 28 due to the irradiation of excitation light and the magnetic force of the magnet 28. Furthermore, in a case where the sixth objective substance 12*f* is not present in the detection liquid 10, since the conjugate 20*f* is not formed, there is no fluorescence resulting from integration of blue fluorescence and green fluorescence moving toward the magnet 28.

In a case where a seventh objective substance 12*g* is present in the detection liquid 10, a conjugate 20*g* of the seventh objective substance 12*g*, the magnetic particles 14, the first labeling particles 16*a*, the second labeling particles 16*b*, and the third labeling particles 16*c* is formed.

As a result, in a case where the seventh objective substance 12*g* is present in the detection liquid 10, fluorescence resulting from integration of red fluorescence, blue fluorescence, and green fluorescence moves toward the magnet 28 due to the irradiation of excitation light and the magnetic force of the magnet 28. Furthermore, in a case where the seventh objective substance 12*g* is not present in the detection liquid 10, since the conjugate 20*g* is not formed, there is no fluorescence resulting from integration of red fluorescence, blue fluorescence, and green fluorescence moving toward the magnet 28.

Therefore, by detecting such movement of fluorescence, detection of the first objective substance 12*a* to the seventh objective substance 12*g* present in the detection liquid 10, that is, the analyte, is enabled by a single detection by a combination of moving fluorescence, that is, a combination of labeling particles bound to the objective substances, as described above.

Furthermore, in the method for detecting an objective substance according to the embodiment of the invention, by increasing the number of kinds of labeling particles in accordance with the third labeling particles 16*c* as necessary, detection of more numerous kinds of objective substances can be carried out by a single detection.

The embodiments shown in FIG. 6 and FIG. 7 can be similarly utilized even in a configuration in which a plurality of kinds of labeling particles satisfy the first condition that the labeling particles are particles the particles having mutually different particle sizes, and a configuration in which a plurality of labeling particles satisfy both the first condition and the second condition.

In the above example, one kind of magnetic particles 14 specifically bind to all of the objective substances; however, the present invention is not limited to this.

That is, in the method for detecting an objective substance according to the embodiment of the invention, regarding the magnetic particles, a plurality of kinds of magnetic particles that specifically bind to one kind of objective substance may be used according to the number of kinds of the objective substance, or a plurality of kinds of magnetic particles that specifically bind to a plurality of kinds of objective substances may be used, or magnetic particles that specifically bind to one kind of objective substance and magnetic particles that specifically bind to a plurality of kinds of objective substances may be used as a mixture. That is, according to the present invention, regarding the binding of the magnetic particles, various embodiments can be utilized so long as the magnetic particles can be caused to specifically bind to all of the objective substances.

The magnetic particles that specifically bind to mutually different objective substances may be the same magnetic particles, or may be different kinds of magnetic particles having different particle sizes, different magnetic forces, different forming materials, and the like.

In this regard, the same applies to the case in which a plurality of kinds of labeling particles satisfy the first condition that the labeling particles are particles having mutually different particle sizes, and the case in which a plurality of labeling particles satisfy both the first condition and the second condition, as will be described later.

Figure 8:
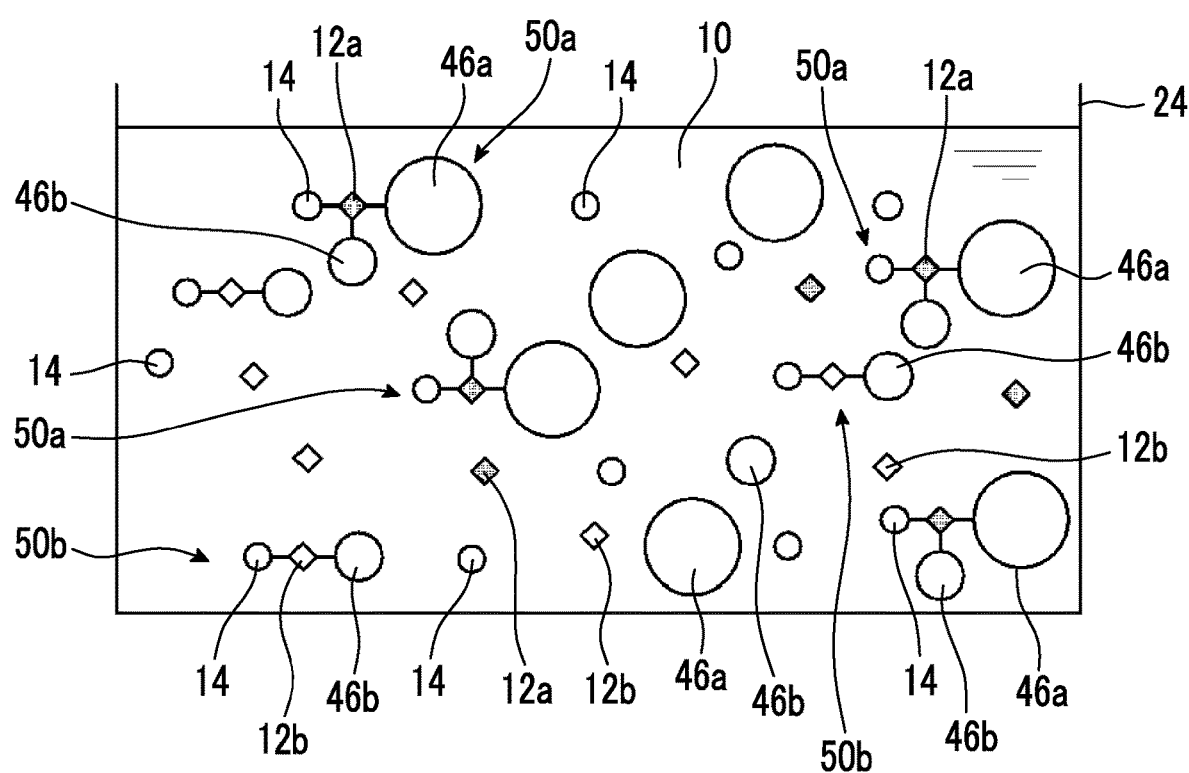
FIG. 8 is a conceptual diagram for explaining another example of the method for detecting an objective substance according to the embodiment of the present invention.

FIG. 8 conceptually shows an example of the detection method according to the embodiment of the invention in a case where a plurality of kinds of labeling particles satisfy the first condition that the particles have mutually different particle sizes.

In the example shown in FIG. 8, the same reference numerals are assigned to the same substances as those shown in FIG. 1 and the like mentioned above, and explanation will be given mainly on different substances.

In the example shown in FIG. 8, the first labeling particles 46*a* and the second labeling particles 46*b* have mutually different particle sizes. In the illustrated example, the first labeling particles 46*a* are larger than the second labeling particles 46*b*. In the following description, the light irradiated to detect the size of the labeling particles will be also referred to as "detection light" for convenience.

As described above, in a case where the plurality of kinds of labeling particles satisfy only the first condition that the particles have mutually different particle sizes, fluorescent particles having the same emission wavelength may be used as the labeling particles.

Furthermore, the first labeling particles 46*a* specifically bind to the first objective substance 12*a*, similarly to the above-mentioned first labeling particles 16*a*. On the other hand, the second labeling particles 46*b* specifically bind to the first objective substance 12*a* and the second objective substance 12*b*, similarly to the above-mentioned second labeling particles 16*b*.

Therefore, an analyte is dissolved in the detection liquid 10 containing the magnetic particles 14, the first labeling particles 46*a*, and the second labeling particles 46*b*, and in a case where the first objective substance 12*a* and the second objective substance 12*b* are supplied, a conjugate 50*a* in which the first objective substance 12*a*, the magnetic particles 14, the first labeling particles 46*a*, and the second labeling particles 46*b* are bound together, and a conjugate 50*b* in which the second objective substance 12*b*, the magnetic particles 14, and the second labeling particles 46*b* are bound together, are formed.

As described above, the first labeling particles 46*a* and the second labeling particles 46*b* are such that the first labeling particles 46*a* are larger than the second labeling particles 46*b*. Therefore, in a case where the detection liquid 10 including the first labeling particles 46*a* and the second labeling particles 46*b* is irradiated with the detection light, two kinds of labeling particles that generate the same signal light as the light but have different particle sizes are observed. In addition, the first labeling particles 46*a* are larger than the second labeling particles 46*b*. In a case where the labeling particles are fluorescent particles, two kinds of same-colored fluorescence having different particle sizes are observed.

In a case where a plurality of kinds of labeling particles satisfy the first condition that the particles have mutually different particle sizes, the first objective substance 12a and the second objective substance 12b can be detected in accordance with the differences in the moving labeling particles and the particle size of these labeling particles, by an action similar to the above-described case of using a plurality of kinds of labeling particles having different emission wavelengths.

In a case where a plurality of kinds of labeling particles satisfy the first condition that the particles have mutually different particle sizes, the difference in the particle size of the labeling particles can be detected as scattered light.

At this time, in a case where the detection liquid 10 including the first labeling particles 46a and the second labeling particles 46b is irradiated with the detection light, two kinds of scattered lights that are the same signal light as the light but have different particle sizes are observed. In addition, the first labeling particles 46a generate larger scattered light than the second labeling particles 46b. In a case where the labeling particles are fluorescent particles, two kinds of fluorescence having different particle sizes are observed.

In a case where a plurality of kinds of labeling particles satisfy the first condition that the particles have mutually different particle sizes and generate scattered light upon being irradiated with the detection light, the first objective substance 12a and the second objective substance 12b can be detected according to the moving scattered light and the difference in the particle size of these scattered lights, by an action similar to the above-described case of using a plurality of kinds of labeling particles having different emission wavelengths.

Specifically, in a case where only the first objective substance 12a is included in the detection liquid 10, that is, the analyte, only the conjugate 50a in which the first objective substance 12a, the magnetic particles 14, the first labeling particles 46a, and the second labeling particles 46b are bound together is formed, and the conjugate 50b in which the second objective substance 12b, the magnetic particles 14, and the second labeling particles 46b are bound together is not formed.

Therefore, in this case, although large labeling particles and small labeling particles are detected upon irradiation with the detection light, the magnetic force of the magnet 28 causes only the conjugate 50a to which the first labeling particles 46a, which are the large labeling particles, and the second labeling particles 46b, which are the small labeling particles, are bound, to move toward the magnet 28.

In a case where only the second objective substance 12b is included in the detection liquid 10, that is, the analyte, only the conjugate 50b in which the second objective substance 12b, the magnetic particles 14, and the second labeling particles 46b are bound together is formed, and the conjugate 50a in which the first objective substance 12a, the magnetic particles 14, the first labeling particles 46a, and the second labeling particles 46b are bound together is not formed.

Therefore, in this case, although large labeling particles and small labeling particles are detected upon irradiation with the detection light, the magnetic force of the magnet 28 causes only the conjugate 50b to which only the second labeling particles 46b, which are the small labeling particles, are bound, to move toward the magnet 28.

In a case where both the first objective substance 12a and the second objective substance 12b are included in the detection liquid 10, that is, the analyte, both the conjugate 50a in which the first objective substance 12a, the magnetic particles 14, the first labeling particles 46a, and the second labeling particles 46b are bound together, and the conjugate 50b in which the second objective substance 12b, the magnetic particles 14, and the second labeling particles 46b are bound together, are formed.

Therefore, in this case, large labeling particles and small labeling particles are detected upon irradiation with the detection light, and the magnetic force of the magnet 28 causes both the conjugate 50a to which the first labeling particles 46a, which are the large labeling particles, and the second labeling particles 46b, which are the small labeling particles, are bound, and the conjugate 50b to which only the second labeling particles 46b, which are the small labeling particles, are bound, to move toward the magnet 28.

Furthermore, in a case where neither the first objective substance 12a nor the second objective substance 12b is included in the analyte, the conjugate 50a and the conjugate 50b are not formed.

Therefore, in this case, although large labeling particles and small labeling particles are detected upon irradiation with the detection light, there are no labeling particles that are caused to move by the magnetic force of the magnet 28.

Therefore, whether the first objective substance 12a and the second objective substance 12b are present can be detected by observing the image picked up by the imaging element 36 or further subjecting the image to an image analysis; detecting the movement of the conjugate 50a to which the first labeling particles 46a, which are large labeling particles, and the second labeling particles 46b, which are small labeling particles, are bound, and the movement of the conjugate 50b to which only the second labeling particles 46b, which are small labeling particles, are bound in the image, or further counting the movement.

That is, according to the present invention of using a plurality of kinds of labeling particles that bind to mutually different objective substances and have mutually different particle sizes, a plurality of kinds of objective substances can be detected by a combination of labeling particles moving by magnetic force, that is, a combination of labeling particles bound to the objective substances.

In this example, regarding the light source 30, a light source that irradiates a detection light that enables observation of the first labeling particles 46a and the second labeling particles 46b is used, and regarding the imaging element 36, an imaging element capable of measuring the detection light emitted from the light source 30 is used.

Regarding the light source 30 and the imaging element 36, various known devices described above can be used so long as they satisfy the above-described conditions.

The image thus picked up by the imaging element 36 may be subjected to image processing. For example, each kind of labeling particles (fluorescence) may be detected by providing a particle diameter filter corresponding to the particle size of each kind of labeling particles, and identifying the particle size using the particle diameter filter. Furthermore, a threshold value may be set for the intensity of light, and then the light exceeding the threshold value may be counted.

Moreover, if necessary, the intensity of the detection light (excitation light) may be changed, and then the labeling particles may be detected or subjected to further counting.

In regard to the above-described point, the process can also be utilized even in a case where the above-mentioned second condition that the signal lights such as fluorescence generated by a plurality of kinds of labeling particles are different, is satisfied.

In a case where a plurality of kinds of labeling particles satisfy the first condition that the particles have mutually different sizes, the size difference between the plurality of kinds of labeling particles is not limited. In a case where a plurality of kinds of labeling particles satisfy the first condition that the particles have mutually different sizes, between labeling particles having particle sizes that are closest to each other, it is preferable that the particle size of larger labeling particles is 2 or more times, more preferably 2.5 or more times, and even more preferably 3 or more times, the particle size of smaller labeling particles.

Between the labeling particles having particle sizes that are closest to each other, by making the difference in the particle size double or more, it becomes possible to more suitably carry out the identification of a plurality of kinds of labeling particles that bind to the objective substances and move, and detection of a plurality of kinds of objective substances can be easily carried out with higher accuracy.

According to the present invention, the particle size of a labeling particle is the maximum length of the labeling particle, that is, the diameter of a smallest sphere that encloses and inscribes the labeling particle. In a case where commercially available particles are used as the labeling particles, the average particle diameter described in a catalog or the like may be used as the particle size of the labeling particles. According to the present invention, the difference in the particle size of the labeling particles may be such that for labeling particles having particle sizes that are closest to each other, the value of at least one of the maximum length or the catalog value of one party is two or more times the value of the other party.

With regard to the method for detecting an objective substance according to the embodiment of the present invention, even in a case where a plurality of kinds of labeling particles satisfy the first condition that the particles have mutually different particle sizes, the detection of an objective substance may be carried out by causing a conjugate to move in one direction only while performing irradiation of light from the light source 30 and image pick-up by the imaging element 36, as shown in FIG. 3; or may be carried out by causing the conjugate to reciprocatingly move while performing irradiation of light from the light source 30 and image pick-up by the imaging element 36, as shown in FIG. 4; or may be carried out by causing the conjugate to move to the magnet 28 side and then performing irradiation of light from the light source 30 and image pick-up by the imaging element 36 at the position to which the conjugate has moved, as shown in FIG. 5.

In this regard, the same applies even to the case where the plurality of kinds of labeling particles satisfy both the first condition and the second condition.

In the above-described example, the detection of an objective substance is carried out by causing the labeling particles to emit fluorescence upon being irradiated with excitation light, or by detecting labeling particles having different particle sizes upon being irradiated with detection light; however, the present invention is not limited to this.

That is, the method for detecting an objective substance according to the embodiment of the present invention is not limited to an irradiation method with light that causes labeling particles to generate signal light and performing detection, as is the case of irradiation of excitation light or the like for causing the labeling particles to emit light, and irradiation of detection light for detecting the labeling particles.

For example, in a case where labeling particles can be directly visually inspected or imaged by means of observation light for observing the interior of the cell 24 without particularly performing irradiation with light for causing generation of signal light, such as the case where the interior of the cell 24 with a fluorescence microscope or the like can be observed, and the case where the image pick-up magnification of the light condensing optical system 38 of the image pick-up unit 40 can be increased, detection of an objective substance may also be carried out by observing the labeling particles using observation light or further image pick-up, without performing irradiation of light for causing the labeling particles to generate signal light.

According to the present invention, in a case where the objective substance is detected using observation light only, the observation light also includes ambient light in the environment in which the cell 24 exists.

The method for detecting an objective substance according to the embodiment of the invention is not limited to a configuration in which a plurality of kinds of labeling particles satisfy only the first condition that the particles have mutually different particle sizes, or a configuration in which the plurality of kinds of labeling particles satisfy only the second condition that the particles generate mutually different signal lights.

That is, in the method for detecting an objective substance according to the embodiment of the invention, a plurality of kinds of labeling particles may satisfy both the first condition that the particles have mutually different sizes, and the second condition that the particles generate mutually different signal lights. Furthermore, in the method for detecting an objective substance according to the embodiment of the invention, among a plurality of kinds of labeling particles, particles that satisfy only the first condition and particles that satisfy the first condition and the second condition may exist as a mixture, or particles that satisfy only the second condition and particles that satisfy the first condition and the second condition may exist as a mixture.

As a plurality of kinds of labeling particles satisfy both the first condition and the second condition, for example, as the movement of fluorescences having different emission wavelengths (colors) and different sizes is detected, detection of a plurality of kinds of objective substances can be carried out, and therefore, detection of objective substances with higher accuracy and high sensitivity is enabled, which is more preferable.

Thus, the method for detecting an objective substance according to the embodiments of the present invention has been described in detail above; however, the present invention is not intended to be limited to the above-mentioned examples, and definitely, various improvements and modifications may be made to the extent that the gist of the present invention is maintained.

EXAMPLES

The features of the present invention will be described more specifically by way of the following Examples. The materials, reagents, amounts of use, amounts of substances, proportions, treatment contents, treatment procedures, and the like shown in the following Examples can be appropriately changed without departing from the spirit of the present invention. Therefore, the scope of the present invention should not be limitedly interpreted by way of the following specific Examples.

Production of Anti-Influenza A Antibody-Modified Magnetic Particles

A mouse monoclonal anti-influenza A (nucleoprotein) antibody was biotin-modified using Biotin Labeling Kit- NH$_2$ (manufactured by Dojindo Molecular Technologies, Inc.), according to the protocol.

Next, anti-influenza A antibody-modified magnetic particles were produced using the biotinylated modified antibody thus obtained and streptavidin-conjugated magnetic particles, Dynabeads MyOne Streptavidin C 1 (manufactured by Thermo Fisher Scientific Inc., average particle diameter 1 μm), according to the protocol.

Production of Anti-Influenza B Antibody-Modified Magnetic Particles

Anti-influenza B antibody-modified magnetic particles were produced in the same manner, except that a mouse monoclonal anti-influenza B (nucleoprotein) antibody was used in place of the mouse monoclonal anti-influenza A (nucleoprotein) antibody.

Production of Anti-Influenza A Antibody-Modified Labeling Particles-A1 (First Labeling Particles)

A mouse monoclonal anti-influenza A (nucleoprotein) antibody (an antibody different from the mouse monoclonal anti-influenza A (nucleoprotein) antibody used in the production of the anti-influenza A antibody-modified magnetic particles was used) was biotin-modified using Biotin Labeling Kit-NH$_2$ (manufactured by Dojindo Molecular Technologies, Inc.), according to the protocol.

Next, anti-influenza A antibody-modified labeling particles-A1 were produced using the biotinylated modified antibody thus obtained and streptavidin-conjugated fluorescent particles, Streptavidin Fluoresbrite YG Microspheres, 6.0 μm (manufactured by Polysciences, Inc., average particle diameter 6 μm), according to the protocol.

These labeling particles are fluorescent particles having an average particle diameter of 6 μm, an excitation wavelength peak of 441 nm, and an emission wavelength peak of 486 nm.

Production of Anti-Influenza A/B Antibody-Modified Labeling Particles-AB1 (Second Labeling Particles)

An antibody responding to mouse monoclonal anti-influenza A (nucleoprotein) and mouse monoclonal anti-influenza B (nucleoprotein) was biotin-modified using Biotin Labeling Kit-NH$_2$ (manufactured by Dojindo Molecular Technologies, Inc.), according to the protocol.

Next, anti-influenza A/B antibody-modified labeling particles-AB1 were produced using the biotinylated modified antibody and streptavidin-conjugated fluorescent particles, Streptavidin Fluoresbrite YG Microspheres, 1.0 μm (manufactured by Polysciences, Inc., average particle diameter 1 μm), according to the protocol.

These labeling particles are fluorescent particles having an average particle diameter of 1 μm, an excitation wavelength peak of 441 nm, and an emission wavelength peak of 486 nm.

Preparation of Detection Liquid-1

The anti-influenza A antibody-modified magnetic particles,
anti-influenza B antibody-modified magnetic particles,
anti-influenza A antibody-modified labeling particles-A1 (average particle diameter 6 μm, excitation wavelength peak 441 nm, emission wavelength peak 486 nm), and
anti-influenza A/B antibody-modified labeling particles-AB1 (average particle diameter 1 μm, excitation wavelength peak 441 nm, emission wavelength peak 486 nm)
thus produced
were dispersed in 1 mL (liter) of PBS, and detection liquid-1 was prepared. The amount of addition of each kind of the particles was $1\times10^7$ particles.

The detection of the objective substance using this detection liquid-1 is to detect an influenza A antigen as a first objective substance and an influenza B antigen as a second objective substance.

Example 1

Detection of Influenza A Nucleoprotein Antigen using Labeling Particles with Different Particle Sizes (First Condition)

A mixed liquid was prepared by adding, to 100 μL of the detection liquid-1 thus prepared, an equal amount of a PBS solution of influenza A nucleoprotein antigen adjusted to a concentration of $1\times10^3$ Plaque Forming Unit (PFU).

Next, the mixed liquid thus obtained was introduced into a cell (Photon Slide Ultra-low Fluorescence Counting Slides, manufactured by Logos Biosystems, Inc.) and was left to stand for 3 minutes.

Next, a permanent magnet was brought close to the cell, and while manually moving the permanent magnet, the interior of the cell was irradiated with excitation light using a blue LED light source (peak wavelength of 440 nm), as conceptually shown in FIG. 2. Furthermore, an excitation light-irradiated region inside the cell was imaged by an image pick-up unit consisting of a general color CCD image sensor, a sharp cutoff filter (transmission limit wavelength 520 nm), and a light condensing optical system.

As a result of analyzing the picked-up image, it was verified that thirty-five integrated green fluorescent particles having a particle size of about 6 μm and a particle size of about 1 μm were moving synchronously with the movement of the permanent magnet. Furthermore, in the detection liquid, no movement of fluorescence was recognized, except for the movement of integrated fluorescent particles having particle sizes of about 6 μm and about 1 μm.

It was verified that thereby, a conjugate of an influenza A nucleoprotein antigen, an anti-influenza A antibody-modified magnetic particles, an anti-influenza A antibody-modified labeling particles-A1 having a particle size of 6 μm, and an anti-influenza A/B antibody-modified labeling particles-AB1 having a particle size of 1 μm was formed in the mixed liquid.

Furthermore, it was also verified that a conjugate of an influenza B nucleoprotein antigen, an anti-influenza B antibody-modified magnetic particles, and an anti-influenza A/B antibody-modified labeling particles-AB1 having a particle size of 1 μm was not formed thereby in the mixed liquid.

As a result, it was verified that an influenza A nucleoprotein antigen was present in the mixed liquid, and an influenza B nucleoprotein antigen was not present therein.

Example 2

Detection of Influenza B Nucleoprotein Antigen using Labeling Particles with Different Particle Sizes (First Condition)

A mixed liquid was prepared by replacing a PBS solution of the influenza A nucleoprotein antigen with the same amount of a PBS solution of the influenza B nucleoprotein antigen at the same concentration.

Detection of the objective substance was carried out in the same manner as in Example 1, except that this mixed liquid was used.

As a result, it was verified that nineteen single green fluorescent particles each having a particle size of about 1 μm were moving synchronously with the movement of the permanent magnet. In the detection liquid, no movement of fluorescent particles was recognized, except for the movement of these single fluorescent particles having a size of about 1 μm.

It was verified that thereby, a conjugate of an influenza B nucleoprotein antigen, an anti-influenza B antibody-modified magnetic particles, and an anti-influenza A/B antibody-modified labeling particles-AB1 having a size of 1 μm was formed in the mixed liquid.

Furthermore, it was also verified that a conjugate of the influenza A nucleoprotein antigen, the anti-influenza A antibody-modified magnetic particles, the anti-influenza A antibody-modified labeling particles-A1 having a particle size of 6 μm, and the anti-influenza A/B antibody-modified labeling particles-AB1 having a particle size of 1 μm was not formed in the mixed liquid.

As a result, it was verified that an influenza B nucleoprotein antigen was present in the mixed liquid, and an influenza A nucleoprotein antigen was not present therein.

Example 3

Detection of Influenza A Nucleoprotein Antigen and Influenza B Nucleoprotein Antigen using Labeling Particles having Different Particle Sizes (First Condition)

A mixed liquid was prepared by adding, to 100 μL of the detection liquid-1 thus prepared, the same amounts of a PBS solution of the influenza A nucleoprotein antigen and a PBS solution of the influenza B nucleoprotein antigen, both adjusted to a concentration of $1 \times 10^3$ PFU.

Detection of the objective substance was carried out in the same manner as in Example 1, except that this mixed liquid was used.

As a result, it was verified that thirty-three integrated green fluorescent particles having a particle size of about 6 μm and a particle size of about 1 μm were moving synchronously with the movement of the permanent magnet, and twenty single green fluorescent particles having a particle size of about 1 μm were moving synchronously with the movement of the permanent magnet.

It was verified that thereby, a conjugate of the influenza A nucleoprotein antigen, the anti-influenza A antibody-modified magnetic particles, the anti-influenza A antibody-modified labeling particles-A1 having a particle size of 6 μm, and the anti-influenza A/B antibody-modified labeling particles-AB1 having a particle size of 1 μm, and a conjugate of the influenza B nucleoprotein antigen, the anti-influenza B antibody-modified magnetic particles, and the anti-influenza A/B antibody-modified labeling particles-AB1 having a particle size of 1 μm, were formed in the mixed liquid.

As a result, it was verified that an influenza A nucleoprotein antigen and an influenza B nucleoprotein antigen were present in the detection liquid.

In addition, Examples 1 to 3 revealed that according to the present invention, the influenza A nucleoprotein antigen and the influenza B nucleoprotein antigen can be detected with high sensitivity.

Production of Anti-Influenza A Antibody-Modified Labeling Particles-A2 (First Labeling Particles)

A mouse monoclonal anti-influenza A (nucleoprotein) antibody (an antibody different from the mouse monoclonal anti-influenza A (nucleoprotein) antibody used in the production of the anti-influenza A antibody-modified magnetic particles was used) was biotin-modified using Biotin Labeling Kit-NH$_2$ (manufactured by Dojindo Molecular Technologies, Inc.), according to the protocol.

Next, anti-influenza A antibody-modified labeling particles-A2 were produced according to the protocol using the biotinylated modified antibody thus obtained and streptavidin-conjugated fluorescent particles, FS Cyanine3 Streptavidin beads (manufactured by Tamagawa Seiki Co., Ltd.).

These labeling particles are fluorescent particles having an average particle diameter of 0.4 μm, an excitation wavelength peak of 550 nm, and an emission wavelength peak of 576 nm.

Production of Anti-Influenza A/B Antibody-Modified Labeling Particles-AB2 (Second Labeling Particles)

An antibody responding to mouse monoclonal anti-influenza A (nucleoprotein) and mouse monoclonal anti-influenza B (nucleoprotein) was biotin-modified using Biotin Labeling Kit-NH$_2$ (manufactured by Dojindo Molecular Technologies, Inc.), according to the protocol.

Next, anti-influenza A/B antibody-modified labeling particles-AB2 were produced according to the protocol using the biotinylated modified antibody thus obtained and streptavidin-conjugated fluorescent particles, FS Cyanine5 Streptavidin beads (manufactured by Tamagawa Seiki Co., Ltd.).

These labeling particles are fluorescent particles having an average particle diameter of 0.4 μm, an excitation wavelength peak of 650 nm, and an emission wavelength peak of 684 nm.

Preparation of Detection Liquid-2

The anti-influenza A antibody-modified magnetic particles,
anti-influenza B antibody-modified magnetic particles,
anti-influenza A antibody-modified labeling particles-A2 (average particle diameter 0.4 μm, excitation wavelength peak 550 nm, emission wavelength peak 576 nm), and
anti-influenza A/B antibody-modified labeling particles-AB2 (average particle diameter 0.4 μm, excitation wavelength peak 650 nm, emission wavelength peak 684 nm)
thus produced
were dispersed in 1 mL of PBS, and detection liquid-2 was prepared. The amount of addition of each kind of the particles was $1 \times 10^7$ particles.

The detection of the objective substance using this detection liquid-2 is to detect an influenza A antigen as the first objective substance and an influenza B antigen as the second objective substance.

Example 4

Detection of Influenza A Nucleoprotein Antigen using Labeling Particles with Different Emission Wavelengths (Second Condition)

To 100 μL of the detection liquid-2 thus prepared, the same amount of a PBS solution of the influenza A nucleoprotein antigen adjusted to a concentration of $1 \times 10^3$ PFU was added.

Next, the mixed liquid thus obtained was introduced into a cell (Photon Slide Ultra-low Fluorescence Counting Slides, manufactured by Logos Biosystems, Inc.) and was left to stand for 3 minutes.

Next, a permanent magnet was brought close to the cell, and while manually moving the permanent magnet, the interior of the cell was irradiated with excitation light from a green LED light source (peak wavelength 510 nm) and a red LED light source (peak wavelength 620 nm), as conceptually shown in FIG. 2. Furthermore, an excitation light-irradiated region inside the cell was imaged by an image pick-up unit consisting of a general color CCD image sensor, a sharp cutoff filter (transmission limit wavelength 560 nm) and a light condensing optical system, and an image pick-up unit consisting of a general color CCD image sensor, a sharp cutoff filter (transmission limit wavelength 660 nm), and a light condensing optical system.

As a result of analyzing the picked-up image, it was verified that thirteen integrated fluorescent particles of orange and red colors were moving synchronously with the movement of the permanent magnet. In addition, other fluorescence in the detection liquid was also recognized; however, only the integrated fluorescent particles of orange and red colors were moving synchronously with the movement of the permanent magnet.

It was verified that thereby, a conjugate of an influenza A nucleoprotein antigen, an anti-influenza A antibody-modified magnetic particles, an anti-influenza A antibody-modified labeling particles-A2 exhibiting orange fluorescence, and an anti-influenza A/B antibody-modified labeling particles-AB2 exhibiting red fluorescence was formed in the mixed liquid.

Furthermore, it was also verified that a conjugate of an influenza B nucleoprotein antigen, an anti-influenza B antibody-modified magnetic particles, and an anti-influenza A/B antibody-modified labeling particles-AB2 exhibiting red fluorescence was not formed thereby in the mixed liquid.

From this, it was verified that an influenza A nucleoprotein antigen was present in the mixed liquid, and an influenza B nucleoprotein antigen was not present therein.

Example 5

Detection of Influenza B Nucleoprotein Antigen using Labeling Particles with Different Emission Wavelengths (Second Condition)

A mixed liquid was prepared by replacing a PBS solution of the influenza A nucleoprotein antigen with the same amount of a PBS solution of the influenza B nucleoprotein antigen at the same concentration.

The objective substance was detected in the same manner as in Example 4, except that this mixed liquid was used.

As a result, it was verified that seventeen single red fluorescent particles were moving synchronously with the movement of the permanent magnet. In addition, other fluorescence in the detection liquid was also recognized; however, only the single red fluorescent particles were moving synchronously with the movement of the permanent magnet.

It was verified that thereby, a conjugate of an influenza B nucleoprotein antigen, an anti-influenza B antibody-modified magnetic particles, and an anti-influenza A/B antibody-modified labeling particles-AB2 exhibiting red fluorescence was formed in the mixed liquid.

It was also verified that a conjugate of an influenza A nucleoprotein antigen, an anti-influenza A antibody-modified magnetic particles, an anti-influenza A antibody-modified labeling particles-A2 exhibiting orange fluorescence, and an anti-influenza A/B antibody-modified labeling particles-AB2 exhibiting red fluorescence was not formed thereby in the mixed liquid.

As a result, it was verified that an influenza B nucleoprotein antigen was present in the mixed liquid, and an influenza A nucleoprotein antigen was not present therein.

Example 6

Detection of Influenza A Nucleoprotein Antigen and Influenza B Nucleoprotein Antigen using Labeling Particles having Different Emission Wavelengths (Second Condition)

A mixed liquid was prepared by adding, to 100 L of the detection liquid-2, thus prepared, the same amounts of a PBS solution of the influenza A nucleoprotein antigen and a PBS solution of the influenza B nucleoprotein antigen, both adjusted to a concentration of $1 \times 10^3$ PFU.

The objective substance was detected in the same manner as in Example 4, except that this mixed liquid was used.

As a result, it was verified that fourteen integrated fluorescent particles of orange and red colors were moving synchronously with the movement of the permanent magnet, and sixteen single red fluorescent particles were moving synchronously with the movement of the permanent magnet.

It was verified that thereby, a conjugate of an influenza A nucleoprotein antigen, an anti-influenza A antibody-modified magnetic particles and an anti-influenza A antibody-modified labeling particles-A2 exhibiting orange fluorescence; a conjugate of an influenza A nucleoprotein antigen, an anti-influenza A antibody-modified magnetic particles and an anti-influenza A/B antibody-modified labeling particles-AB2 exhibiting red fluorescence; and a conjugate of an influenza B nucleoprotein antigen, an anti-influenza B antibody-modified magnetic particles, and an anti-influenza A/B antibody-modified labeling particles-AB2 exhibiting red fluorescence was formed in the mixed liquid.

As a result, it was verified that an influenza A nucleoprotein antigen and an influenza B nucleoprotein antigen were present in the mixed liquid.

In addition, Examples 4 to 6 revealed that according to the present invention, the influenza A nucleoprotein antigen and the influenza B nucleoprotein antigen can be detected with high sensitivity.

Production of Anti-Adenovirus Antibody-Modified Magnetic Particles

Anti-adenovirus antibody-modified magnetic particles were produced in the same manner, except that a mouse monoclonal anti-adenovirus antibody was used instead of the mouse monoclonal anti-influenza A (nucleoprotein) antibody.

Production of Anti-Adenovirus/Anti-Influenza A Antibody-Modified Labeling Particles (Third Labeling Particles)

An antibody reacting toward mouse monoclonal anti-adenovirus and mouse monoclonal anti-influenza A (nucleoprotein) was biotin-modified using Biotin Labeling Kit-NH$_2$ (manufactured by Dojindo Molecular Technologies, Inc.), according to the protocol.

Next, anti-adenovirus/anti-influenza A antibody-modified labeling particles were produced according to the protocol using the biotinylated modified antibody thus obtained and streptavidin-conjugated fluorescent particles, FS Eu Streptavidin beads (manufactured by Tamagawa Seiki Co., Ltd.).

These labeling particles are fluorescent particles having an average particle diameter of 0.4 µm, an excitation wavelength peak of 340 nm, and an emission wavelength peak of 616 nm.

Preparation of Detection Liquid-3

The anti-influenza A antibody-modified magnetic particles,
  anti-influenza B antibody-modified magnetic particles,
  anti-adenovirus antibody-modified magnetic particles,
  anti-influenza A antibody-modified labeling particles-A1 (average particle diameter 6 µm, excitation wavelength peak 441 nm, emission wavelength peak 486 nm),
  anti-influenza A/B antibody-modified labeling particles-AB1 (average particle diameter 1 µm, excitation wavelength peak 441 nm, emission wavelength peak 486 nm), and
  anti-adenovirus/anti-influenza A antibody-modified labeling particles (average particle diameter 0.4 µm, excitation wavelength peak 340 nm, emission wavelength peak 616 nm)
thus produced
were dispersed in 1 mL (liter) of PBS, and detection liquid-3 was prepared. The amount of addition of each kind of the particles was $1 \times 10^7$ particles.

The detection of the objective substance using this detection liquid-3 is to detect the influenza A antigen as the first objective substance, the influenza B antigen as the second objective substance, and the adenovirus antigen as the third objective substance.

Example 7

Detection of Influenza A Antigen using Labeling Particles with Different Particle Sizes (First Condition) and Labeling Particles with Different Emission Wavelengths (Second Condition)

A mixed liquid was prepared by adding, to 100 µL of the detection liquid-3 thus prepared, the same amount of a PBS solution of the influenza A nucleoprotein antigen adjusted to a concentration of $1 \times 10^3$ PFU.

Next, the mixed liquid thus obtained was introduced into a cell (Photon Slide Ultra-low Fluorescence Counting Slides, manufactured by Logos Biosystems, Inc.) and was left to stand for 3 minutes.

Then, the permanent magnet was brought close to the cell, and while manually moving the permanent magnet, the interior of the cell was irradiated with excitation light from a blue LED light source (peak wavelength 440 nm) and an ultraviolet LED light source (peak wavelength 340 nm), as conceptually shown in FIG. 2. Furthermore, an excitation light-irradiated region inside the cell was imaged by an image pick-up unit consisting of a general color CCD image sensor, a sharp cutoff filter (transmission limit wavelength 520 nm), and a light condensing optical system.

As a result of analyzing the picked-up image, it was verified that green fluorescent particles having a particle size of about 6 µm, green fluorescent particles having a particle size of about 1 µm, and red fluorescent particles having a particle size of about 0.4 µm were integrated, and sixteen integrated fluorescent particles were moving synchronously with the movement of the permanent magnet. In the detection liquid, no movement of fluorescent particles was recognized, except for the movement of these integrated fluorescent particles.

It was verified that thereby, a conjugate of an influenza A nucleoprotein antigen, an anti-influenza A antibody-modified magnetic particles, an anti-influenza A antibody-modified labeling particles-A1 having a particle size of 6 µm and exhibiting green fluorescence and an anti-influenza A/B antibody-modified labeling particles-AB1 having a particle size of 1 µm and exhibiting green fluorescence, and an anti-adenovirus/anti-influenza A antibody-modified labeling particles having a particle size of 0.4 µm and exhibiting red fluorescence, was formed in the mixed liquid.

It was also verified that a conjugate of an influenza B nucleoprotein antigen, an anti-influenza B antibody-modified magnetic particles, and an anti-influenza A/B antibody-modified labeling particles-AB1 having a particle size of 1 µm and exhibiting green fluorescence, and a conjugate of an adenovirus antigen, an anti-adenovirus antibody-modified magnetic particles, and an anti-adenovirus/anti-influenza A antibody-modified labeling particles having a particle size of 0.4 µm and exhibiting red fluorescence, was not formed thereby in the mixed liquid.

As a result, it was verified that an influenza A nucleoprotein antigen was present in the mixed liquid, and an influenza B nucleoprotein antigen and an adenovirus antigen were not present therein.

Example 7 revealed that according to the present invention, an influenza A nucleoprotein antigen can be detected with high sensitivity.

From the above results, the effect of the present invention is obvious.

The invention can be suitably utilized for the detection of viruses and the like in medical care and research.

EXPLANATION OF REFERENCES

10: Detection liquid
12a: First objective substance
12b: Second objective substance
12c: Third objective substance
12d: Fourth objective substance
12e: Fifth objective substance
12f: Sixth objective substance
12g: Seventh objective substance
14: Magnetic particles
16a, 46a: First labeling particles
16b, 46b: Second labeling particles
16c: Third labeling particles
20a, 20b, 50a, 50b: Conjugate
24: Cell
28: Magnet
30: Light source
32, 38: Light condensing optical system
34: Excitation light irradiation unit
36: Imaging element
40: Image pick-up unit

What is claimed is:

1. A method for detecting an objective substance by causing magnetic particles and labeling particles to bind to the objective substance and causing a conjugate of the objective substance, magnetic particles, and labeling particles to move by magnetic force, the method comprising:
  detecting at least a first objective substance, a second objective substance, and a third objective substance as the objective substance, each of the magnetic particles being capable of binding to the first objective substance, the second objective substance, and the third objective substance, using first labeling particles capable of binding to the first objective substance and the third objective substance but not to the second objective substance, and second labeling particles capable of binding to the first objective substance and the second objective substance but not to the third objective substance, the first labeling particles and the second labeling particles satisfying at least one of a first condition that the first labeling particles and the second labeling particles have mutually different particle sizes or a second condition that the first labeling particles and the second labeling particles generate signal lights upon being irradiated with light and the signal lights are mutually different;

supplying the first objective substance, the second objective substance, the third objective substance, the first labeling particles, the second labeling particles, and the magnetic particles to a detection liquid to cause the conjugate in which at least one of the first labeling particle and the second labeling particle, and the magnetic particles are bound to the first objective substance, the second objective substance, and the third objective substance, and moving the conjugate by magnetic force to detect the objective substance by at least one of the particle size and the signal lights of the first labeling particles and the second labeling particles bound to the first objective substance, the second objective substance, and/or the third objective substance.

2. The method for detecting an objective substance according to claim 1,
wherein in a case where the first labeling particles and the second labeling particles satisfy the first condition, the particle size of the larger labeling particle is two or more times the particle size of the smaller labeling particle.

3. The method for detecting an objective substance according to claim 1,
wherein in a case where the first labeling particles and the second labeling particles satisfy the second condition, the first labeling particles and the second labeling particles are particles that emit light upon being irradiated with light, and a difference in emission wavelength is 15 nm or more.

4. The method for detecting an objective substance according to claim 1,
wherein the first labeling particles and the second labeling particles satisfy both the first condition and the second condition.

5. The method for detecting an objective substance according to claim 1,
wherein the detection of the first objective substance, the second objective substance, and the third objective substance is carried out by irradiation with light that causes the first labeling particles and the second labeling particles to generate the signal lights.

6. The method for detecting an objective substance according to claim 1,
wherein the detection of the first objective substance, the second objective substance, and the third objective substance is carried out by enlarging a detection field of view for the first objective substance, the second objective substance, and the third objective substance and using observation light for observing a detection position of the first objective substance, the second objective substance, and the third objective substance.

7. The method for detecting an objective substance according to claim 1,
wherein the detection of the first objective substance, the second objective substance, and the third objective substance is carried out while causing the conjugate to move by the magnetic force.

8. The method for detecting an objective substance according to claim 1,
wherein the detection of the first objective substance, the second objective substance, and the third objective substance is carried out after causing the conjugate to move by the magnetic force.

9. The method for detecting an objective substance according to claim 1,
wherein at least one of the first labeling particles or the second labeling particles is modified with a plurality of antibodies, at least one of the first labeling particles or the second labeling particles has at least one of a plurality of receptors or a plurality of ligands, bound thereto, or at least one of the first labeling particles or the second labeling particles is modified with one or more antibodies and has one or more of at least one of receptors or ligands, bound thereto.

10. The method for detecting an objective substance according to claim 1,
the method comprising further using third labeling particles that do not bind to the first objective substance, the second objective substance, and the third objective substance and are capable of binding to another objective substance than the first objective substance, the second objective substance, and the third objective substance.

11. The method for detecting an objective substance according to claim 10,
wherein the third labeling particles is capable of binding to one kind of an objective substance to which the first labeling particles and the second labeling particles are incapable of binding.

12. The method for detecting an objective substance according to claim 10,
wherein each of the first labeling particles, the second labeling particles, and the third labeling particles is incapable of binding to one kind of an objective substance to which the other two labeling particles are capable of binding.

13. The method for detecting an objective substance according to claim 10,
wherein the first labeling particles, the second labeling particles, and the third labeling particles are capable of binding to one kind of the same objective substance.

\* \* \* \* \*